US007510719B2

(12) United States Patent
Dang et al.

(10) Patent No.: US 7,510,719 B2
(45) Date of Patent: Mar. 31, 2009

(54) METHODS OF PRODUCING INFLUENZA VACCINE COMPOSITIONS

(75) Inventors: Qi Dang, Union City, CA (US); Richard Schwartz, San Mateo, CA (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 11/295,437

(22) Filed: Dec. 7, 2005

(65) Prior Publication Data

US 2006/0153872 A1 Jul. 13, 2006

Related U.S. Application Data

(60) Provisional application No. 60/634,690, filed on Dec. 8, 2004.

(51) Int. Cl.
A61K 39/145 (2006.01)
A61K 39/00 (2006.01)
A61K 39/295 (2006.01)
A61K 39/12 (2006.01)
C12P 21/04 (2006.01)
A61K 39/20 (2006.01)

(52) U.S. Cl. .............. 424/206.1; 424/209.1; 424/184.1; 424/202.1; 424/205.1; 435/70.1

(58) Field of Classification Search ........................ None
See application file for complete search history.

(56) References Cited

U.S. PATENT DOCUMENTS

| 4,500,513 | A | 2/1985 | Brown et al. | |
|---|---|---|---|---|
| 6,146,873 | A | 11/2000 | Kistner et al. | |
| 6,455,298 | B1 | 9/2002 | Groner et al. | |
| 6,544,785 | B1 | 4/2003 | Palese et al. | |
| 6,649,372 | B1 | 11/2003 | Palese et al. | |
| 6,656,720 | B2 | 12/2003 | Groner et al. | |
| 6,824,784 | B2 * | 11/2004 | Dowling et al. | 424/209.1 |
| 6,951,754 | B2 | 10/2005 | Hoffmann | |
| 2003/0035814 | A1 | 2/2003 | Kawaoka et al. | |
| 2004/0029251 | A1 | 2/2004 | Hoffmann et al. | |
| 2004/0265987 | A1 | 12/2004 | Trager et al. | |
| 2005/0158342 | A1 | 7/2005 | Kemble et al. | |
| 2005/0266026 | A1 | 12/2005 | Hoffmann et al. | |
| 2006/0110406 | A1 | 5/2006 | Kemble et al. | |

FOREIGN PATENT DOCUMENTS

| EP | 1 526 172 A1 | 4/2005 |
|---|---|---|
| EP | 0 891 420 B1 | 5/2005 |
| WO | WO-99-28445 A1 | 6/1999 |
| WO | WO-01-38362 A2 | 5/2001 |
| WO | WO-03-091401 A2 | 11/2003 |

OTHER PUBLICATIONS

Keck et al., Temperature Profile in the Nasal Cavity, 2000, Laryngoscope, vol. 110, pp. 651-654.*
Kiseleva et al., Cell-based assay for the determination of temperature sensitive and cold adapted phenotypes of influenza viruses, 2004, Journal of Virological Methods, vol. 116, pp. 71-78.*
Yannarell et al., Factors affecting the yield of cold-adapted influenza virus vaccine, 1997, Jouranl of Virological Methods, vol. 64, pp. 161-169.*
International Search Report PCT/US05/44267. (2006).
Written Report PCT/US05/44267. (2006).
Furminger, I. "Vaccine Production." Textbook of Influenza., 1998. 324-332.
Maassab, H. F. "Adaptation and Growth Characteristics of Influenza Virus at 25 Degrees c." Nature (1967) 76: 612-4.
Merten, O.W. et al. "Production of Influenza Virus in Cell Cultures for Vaccine Preparation." Novel Strategies in Design and Production of Vaccines., 1996.
Murphy, B. R., et al. "Principles Underlying the Development and use of Live Attenuated Cold-Adapted Influenza A and B Virus Vaccines." Viral Immunol. (2002) 2: 295-323.
Obrosova-Serova, N. P., et al. "Evaluation in Children of ca Influenza B Live att Intranasal Vaccine . . . ." Vaccine (1990) 1: 57-60.
Wareing, M. D., et al. "Preparation and Characterisation of att ca Influenza A Reassortants Derived from the A/Leningrad/134/17/57 Donor Strain." Vaccine (2002) 16: 2082-90.
Youil, R., et al. "Phenotypic and Genetic Analyses of . . . A/Leningrad/134/17/57 (H2N2)." Virus Res. (2004) 2: 165-76.
Alexandrova, G. I., et al. "Lab. Properties of ca Influenza B Live Vaccine Strains . . . and their B/Ann Arbor/1/86 ca Reassortant Vaccine Candidates." Vaccine (1990) 1:61-4.
Maassab & Deborde, Characterization of an influenza A host range mutant. Virology, 130(2):342-50 (1983).
Hoffmann et al., Eight-plasmid system for rapid generation of influenza virus vaccines. Vaccine, 20:3165-3170 (2002).
Rudneva et al., Effect of gene constellation and postreassortment amino acid change on the phenotypic features of H5 influenza virus reassortants. Arch Virol, 152(6):1139-45 (2007).
Condit, C.R., Principles of Virology., Fields Virology, Lippincott Williams & Wilkins, 5th Edition, Chapter 2, p. 25-57 (2007).
Snyder et al., The avian influenza virus nucleoprotein gene and a specific constellation of avian and human virus polymerase genes each specify attenuation of avian-human influenza A/Pintail/79 reassortant viruses for monkeys. Journal of Virology, 61:2857-2863 (1987).
Lugotsev et al., Generation of the influenza B viruses with improved growth phenotype by substitution of specific amino acids of hemagglutinin. Virology, doi.:10.1016/j.virol.2007.04.006 (2007).
Vodeiko et al., Genetic and phenotypic analysis of reassortants of high growth and low growth strains of influenza B virus. Vaccine, 21:3867-3874 (2003).
Murphy et al., Temperature-sensitive mutants of influenza virus. 3. Further characterization of the ts-1(E) influenza A recombinant (H3N2) virus in man. The Journal of Infectious Diseases, 128(4):479-487 (1973).

(Continued)

*Primary Examiner*—Bruce Campell
*Assistant Examiner*—Benjamin P Blumel

(57) ABSTRACT

Methods and compositions for the optimization and production of influenza viruses, e.g., ca influenza B strains, in eggs and host cells suitable as influenza vaccines are provided.

12 Claims, 13 Drawing Sheets

OTHER PUBLICATIONS

Dauber et al., The influenza B virus nonstructural NS1 protein is essential for efficient viral growth and antagonizes beta interferon induction. Journal of Virology, 78(4):1865-1872 (2004).

Lugotsev et al., Mutational pattern of influenza B viruses adapted to high growth replication in embryonated eggs. Virus Research 109:149-157 (2005).

Hughes et al., Yield increases in intact influenza vaccine virus from chicken allantoic fluid through isolation from insoluble allantoic debris. Vaccine, 25:4456-4463 (2007).

Richard Condit "Principles of Virology." Field's virology (2007) chapeter 2, pp. 25-57, Lippincott Williams & Wilkins (Philadelphia).

* cited by examiner

| ca Strains | Titer ($\log_{10}$ TCID$_{50}$/mL) | | | | | | | |
|---|---|---|---|---|---|---|---|---|
| | Temperature (± 0.5°C) | | | | | | | |
| | 28°C | 29°C | 30°C | 31°C | 32°C | 33°C | 34°C | 35°C |
| B/Ann Arbor/1/66 (MDV) | NT | ND[1] | NT | 7.3 | NT | 7.4 | NT | NT |
| B/Victoria/504/2000 | 7.2 | NT | NT | 8.4 | NT | 7.7 | 6.7 | NT |
| B/Johannesburg/5/99 | NT | 6.9 | NT | 8.6 | NT | 8.3 | NT | 7.3 |
| B/Brisbane/32/2002 | NT | 7.3 | NT | 8.9 | NT | 8.6 | NT | 7.6 |
| B/Ann Arbor/1/94 | NT | 8.3 | NT | 8.6 | NT | 8.4 | NT | NT |
| B/Beijing/243/97 | NT | 8.9 | NT | 9.1 | NT | 8.9 | NT | NT |
| B/Hong Kong 330/01 | NT | 9.0 | NT | 9.1 | NT | 8.7 | NT | NT |
| B/Yanamashi/166/98 | NT | 8.6 | NT | 8.8 | NT | 8.4 | NT | NT |
| B/Jilin/20/03 (16Apr04) | NT | 7.2 | NT | 8.4 | NT | 7.7 | 6.7 | NT |
| B/Jilin/20/03 (06May04) | NT | NT | 8.3 | 8.6 | 8.1 | 8.2 | NT | NT |
| B/Jilin/20/03 (28May04) | NT | 7.7 | 8.3 | 8.4 | 8.2 | NT | NT | NT |

NT, Not Tested, [1] Titer <6.7 $\log_{10}$ TCID$_{50}$/mL

Fig. 1

| Vaccine Virus | Titer at 25°C | Titer at 33°C | Titer at 37°C | $Log_{10}$ differential 25/33 | $Log_{10}$ differential 37/33 |
|---|---|---|---|---|---|
| ca B/Ann Arbor/01/94 grown at 29°C Z0015 PD, 72hr, 11Jun04. | 7.6 ± 0.1 | 7.3 ± 0.1 | 3.7 ± 0.0 | 0.3 | 3.6 |
| ca B/Ann Arbor/01/94 grown at 31°C Z0015 PD, 72hr, 11Jun04 | 8.1 ± 0.1 | 7.7 ± 0.0 | 4.2 ± 0.0 | 0.4 | 3.5 |
| ca B/Ann Arbor/01/94 grown at 33°C Z0015 PD, 72hr, 11Jun04. | 7.6 ± 0.1 | 7.5 ± 0.1 | 4.2 ± 0.0 | 0.1 | 3.3 |
| ca B/Beijing/243/97 grown at 29°C Z0015 PD, 72hr, 11Jun04. | 8.6 ± 0.1 | 8.3 ± 0.1 | 4.2 ± 0.0 | 0.3 | 4.1 |
| ca B/Beijing/243/97 grown at 31°C Z0015 PD, 72hr, 11Jun04. | 8.8 ± 0.1 | 8.9 v 0.0 | 4.7 ± 0.0 | 0.1 | 4.2 |
| ca B/Beijing/243/97 grown at 33°C Z0015 PD, 72hr, 11Jun04. | 8.4 ± 0.0 | 8.2 ± 0.0 | 4.2 ± 0.0 | 0.2 | 4.0 |
| ca B/HongKong/330/01 grown at 29°C Z0015 PD, 72hr, 11Jun04. | 8.7 ± 0.0 | 8.4 ± 0.0 | 4.2 ± 0.0 | 0.3 | 4.2 |
| ca B/HongKong/330/01 grown at 31°C Z0015 PD, 72hr, 11Jun04. | 8.9 ± 0.2 | 8.1 ± 0.1 | 4.3 ± 0.1 | 0.8 | 3.8 |
| ca B/HongKong/330/01 grown at 33°C Z0015 PD, 72hr, 11Jun04. | 8.5 ± 0.1 | 7.8 ± 0.1 | 4.2 ± 0.0 | 0.7 | 3.6 |
| ca B/Yamanashi/166/98 grown at 29°C Z0015 PD, 72hr, 11Jun04. | 8.3 ± 0.1 | 8.3 ± 0.1 | 3.9 ± 0.0 | 0.0 | 4.4 |
| ca B/Yamanashi/166/98 grown at 31°C Z0015 PD, 72hr, 11Jun04. | 8.8 ± 0.1 | 8.8 ± 0.1 | 4.5 ± 0.0 | 0.0 | 4.3 |
| ca B/Yamanashi/166/98 grown at 33°C Z0015 PD, 72hr, 11Jun04. | 8.4 ± 0.2 | 7.9 ± 0.2 | 4.2 ± 0.0 | 0.5 | 3.7 |
| B/Jilin/20/03 grown at 31°C Dev. Lot: Z0015 PD 16Apr04, DQ NB 773 | 8.1 ± 0.1 | 7.5 ± 0.1 | 4.1 ± 0.1 | 0.6 | 3.4 |
| B/Jilin/20/03 grown at 31°C 600050-A – 31°C lot (bulk manufacture) | 7.4 | 6.3 | <2.7 | 1.1 | >3.6 |
| B/Jilin/20/03 grown at 33°C Dev Lot: Z0015 PD 16Apr04, DQ NB 773 | 7.6 ± 0.2 | 7.2 ± 0.2 | 3.2 ± 0.0 | 0.4 | 4.0 |
| B/Jilin/20/03 grown at 31°C 600054-B – 31°C lot (bulk manufacture) | 7.5 | 6.9 | <3.7 | 0.6 | >3.2 |

Fig. 4

| ca Strains | HA Titer (HAU) | | | | | | | |
|---|---|---|---|---|---|---|---|---|
| | Temperature (± 0.5°C) | | | | | | | |
| | 28°C | 29°C | 30°C | 31°C | 32°C | 33°C | 34°C | 35°C |
| B/Ann Arbor/1/66 (MDV) | NT | <2 | NT | 32 | NT | 16 | NT | NT |
| B/Victoria/504/2000 | 0 | NT | NT | 256 | NT | 64 | 32 | NT |
| B/Johannesburg/5/99 | NT | 0 | NT | 64 | NT | 32 | NT | 0 |
| B/Brisbane/32/2002 | NT | 0 | NT | 128 | NT | 64 | NT | 0 |
| B/Ann Arbor/1/94 | NT | 4 | NT | 32 | NT | 16 | NT | NT |
| B/Beijing/243/97 | NT | 32 | NT | 64 | NT | 32 | NT | NT |
| B/Hong Kong 330/01 | NT | 32 | NT | 64 | NT | 32 | NT | NT |
| B/Yanamashi/166/98 | NT | 64 | NT | 128 | NT | 64 | NT | NT |
| B/Jilin/20/03 (16Apr04) | NT | 0 | NT | 32 | NT | 8 | NT | NT |
| B/Jilin/20/03 (06May04) | NT | NT | 8 | 64 | 8 | 16 | NT | NT |
| B/Jilin/20/03 (28May04) | NT | 8 | 128 | 256 | 128 | NT | NT | NT |

NT, Not Tested

Fig. 5

| ca Strains | Gene Segment (HA) Copy Number (log$_{10}$ / mL) | | | | | | | |
|---|---|---|---|---|---|---|---|---|
| | Temperature (± 0.5°C) | | | | | | | |
| | 28°C | 29°C | 30°C | 31°C | 32°C | 33°C | 34°C | 35°C |
| B/Ann Arbor/1/66 (MDV) | NT | NT | NT | 9.0 | NT | 8.7 | NT | NT |
| B/Victoria/504/2000 | 8 | NT | NT | 10.1 | NT | 9.5 | 9.1 | NT |
| B/Johannesburg/5/99 | NT | 7.7 | NT | 9.7 | NT | 9.6 | NT | 8.7 |
| B/Brisbane/32/2002 | NT | 8.1 | NT | 9.8 | NT | 9.7 | NT | 8.7 |
| B/Ann Arbor/1/94 | NT | 9.0 | NT | 9.6 | NT | 9.4 | NT | NT |
| B/Beijing/243/97 | NT | 9.6 | NT | 10.0 | NT | 9.7 | NT | NT |
| B/Hong Kong 330/01 | NT | 9.6 | NT | 10.0 | NT | 9.6 | NT | NT |
| B/Yanamashi/166/98 | NT | 9.6 | NT | 9.8 | NT | 9.7 | NT | NT |
| B/Jilin/20/03 (16Apr04) | NT | 8.4 | NT | 9.8 | NT | 9.1 | 8.1 | NT |
| B/Jilin/20/03 (06May04) | NT | NT | NT | 9.8 | NT | 9.6 | NT | NT |
| B/Jilin/20/03 (28May04) | NT | 9.2 | 9.8 | 9.9 | 9.8 | NT | NT | NT |

NT, Not Tested

Fig. 6

| ca Strains | HA Gene Copy Number (log$_{10}$):Potency Ratio (log$_{10}$) (Copy Number log$_{10}$/mL - log$_{10}$ TCID$_{50}$/mL) | |
|---|---|---|
| | Temperature (± 0.5°C) | |
| | 33°C | 31°C |
| B/Ann Arbor/1/66 (MDV) | 1.3 | 1.1 |
| B/Victoria/504/2000 | 1.8 | 1.7 |
| B/Johannesburg/5/99 | 1.3 | 1.1 |
| B/Brisbane/32/2002 | 1.1 | 0.9 |
| B/Ann Arbor/1/94 | 1.1 | 1.0 |
| B/Beijing/243/97 | 0.9 | 0.9 |
| B/Hong Kong 330/01 | 0.9 | 0.9 |
| B/Yanamashi/166/98 | 1.3 | 1.0 |
| B/Jilin/20/03 (16Apr04) | 1.4 | 1.4 |
| B/Jilin/20/03 (06May04) | 1.4 | 1.2 |
| B/Jilin/20/03 (28May04) | 1.4 | 1.4 |

Fig. 7

| Virus | Growth Temp. (°C) | Titer (log$_{10}$TCID$_{50}$/mL) | Total Particle (log$_{10}$) /mL | %Infec. Particle |
|---|---|---|---|---|
| ca B/Jilin/20/03 | 31 | 8.4 | 9.9 | 3.3 |
|  | 33 | 7.7 | 9.3 | 2.3 |
| ca B/AnnArbor/01/94 (B/Harbin-like) | 31 | 8.6 | 9.9 | 4.5 |
|  | 33 | 8.3 | 9.7 | 4.2 |

Fig. 8

| Ca B/Jilin/20/03 | | | |
|---|---|---|---|
| | Grown at 33°C | Grown at 31°C | |
| Reference Sequence. (MVS Lot No. 0141900073) | Development Lot Z0015 PD 16Apr04, DQ NB 773 | Development Lot Z0015 PD 16Apr04, DQ NB 773 | Bulk Manufacture Batch No. 600054C |
| PB1 | Identical | Identical | Identical |
| PB2 | Identical | Identical | Identical |
| PA | Identical | Identical | Identical |
| HA | Identical | Identical | Identical |
| NP | Identical | Identical | Identical |
| NA | Identical | Identical | Identical |
| M | Identical | Identical | Identical |
| NS | Identical | Identical | Identical |

Fig. 9

| | HAI Titer log$_2$ GMT±SD (n=2) |
|---|---|
| *ca* B/Jilin/20/03 Grown at 31°C<br>Z0015 PD 16Apr04, DQ NB 773 | 7.0 ± 0.0 |
| *ca* B/Jilin/20/03 Grown at 33°C<br>Z0015 PD 16Apr04, DQ NB 773 | 7.0 ± 0.0 |

Fig. 10

| Inoculum | Dose (Log$_{10}$ TCID$_{50}$) | N | HAI Titer log$_2$ GMT±SD |
|---|---|---|---|
| ca B/Jilin/20/03 Grown at 31°C | 7.0 | 5 | 5.2 ± 0.4 |
| ca B/Jilin/20/03 Grown at 33°C Z0015 PD 16Apr04, DQ NB 773 | 7.0 | 5 | 5.2 ± 0.4 |

Fig. 12

METHODS OF PRODUCING INFLUENZA VACCINE COMPOSITIONS

CROSS REFERENCE TO RELATED APPLICATIONS

This application claims the benefit under 35 U.S.C. §119 (e) of the following U.S. Provisional Application No. 60/634,690 filed Dec. 8, 2004. The priority application is hereby incorporated by reference herein in its entirety for all purposes.

BACKGROUND OF THE INVENTION

Vaccines against various and evolving strains of influenza are important not only from a community health stand point, but also commercially, since each year numerous individuals are infected with different strains and types of influenza virus. Infants, the elderly, those without adequate health care and immuno-compromised persons are at special risk of death from such infections. Compounding the problem of influenza infections is that novel influenza strains evolve readily, thereby necessitating the continuous production of new vaccines.

Numerous vaccines capable of producing a protective immune response specific for such different influenza viruses have been produced for over 50 years and include, e.g., whole virus vaccines, split virus vaccines, surface antigen vaccines and live attenuated virus vaccines. However, while appropriate formulations of any of these vaccine types are capable of producing a systemic immune response, live attenuated virus vaccines have the advantage of being also able to stimulate local mucosal immunity in the respiratory tract. A vaccine comprising a live attenuated virus that is capable of being quickly and economically produced and that is capable of easy storage/transport is thus quite desirable. Also desirable would be methods to increase production of such viruses, and thus of vaccines for such viruses, especially for virus strains that have proven difficult to produce and/or scale up for commercial production using traditional methods.

To date, all commercially available influenza vaccines in the United States have been propagated in embryonated hen eggs. Although many influenza virus strains grow well in hen eggs, the production of vaccine is dependent on the availability of such eggs. Because the supply of eggs must be organized, and strains for vaccine production selected months in advance of the next flu season, the flexibility of this approach can be limited, and often results in delays and shortages in production and distribution. Also, various influenza virus strains grow less well in eggs (e.g., do not produce as high a titer) as other influenza strains. Therefore, methods to increase production, e.g., of desired strains of such viruses, and thus vaccines, are greatly desirable.

Systems for producing influenza viruses in cell culture have also been developed in recent years (See, e.g., Furminger. Vaccine Production, in Nicholson et al. (eds.) Textbook of Influenza pp. 324-332; Merten et al. (1996) Production of influenza virus in cell cultures for vaccine preparation, in Cohen & Shafferman (eds.) Novel Strategies in Design and Production of Vaccines pp. 141-151). However, such systems can also involve production or scale-ups in eggs and so can also encounter productivity issues, especially in regard to specific strains. Therefore, any methods to increase virus/vaccine production in these systems as well are also greatly desirable.

Considerable work in the production of influenza virus for production of vaccines has been done by the present inventor and co-workers; see, e.g., PCT Publications WO 03/091401, WO 05/014862, and PCT Patent Applications PCT/US05/017734, filed May 20, 2005, and PCT/US05/035614, filed Oct. 4, 2005. The present invention provides methods of increasing production of influenza viruses and virus compositions for production of vaccine compositions. Aspects of the current invention are applicable to traditional hen egg and new cell culture vaccine production styles (and also combined systems) that comprise steps of virus growth in hen eggs, and comprise numerous other benefits that will become apparent upon review of the following.

SUMMARY OF THE INVENTION

The current invention comprises methods of producing influenza virus particles by introducing a plurality of vectors (e.g., plasmids, viruses, etc., see below) comprising or encoding an influenza virus genome or partial genome, into one or more host eggs or other host cells (e.g., MDCK and Vero) and incubating the host eggs or other host cells (e.g., MDCK and Vero) at a temperature below 33° C.; and, recovering the influenza virus particles from the host eggs or other host cells (e.g., MDCK and Vero). The present invention also encompasses methods of increasing the yield of influenza virus particles comprising incubating said virus particles at a temperature below 33° C. (e.g., 31° C.) in host cells (e.g., a continuous cell culture of MDCK or Vero cells) or embryonated eggs. In certain embodiments the $\log_{10}$ $TCID_{50}$/mL titer of virus particles produced at a temperature below 33° C. is greater than that of the same virus particles produced at 33° C. In other embodiments, the methods of the present invention include introducing influenza virus (e.g., a reassortant virus) into one or more embryonated eggs that are capable of supporting replication of influenza virus, thereby infecting said embryonated eggs. In still other embodiment, the methods of the present invention include introducing influenza virus (e.g., a reassortant virus) into host cells (e.g., MDCK and Vero) that are capable of supporting replication of influenza virus, thereby infecting said host cells. The virus produced can be an influenza B strain virus, an attenuated influenza virus, a cold adapted influenza virus, a temperature sensitive influenza virus, an attenuated cold adapted temperature sensitive influenza virus, or any combinations thereof. In some embodiments, the virus comprises a PR8 backbone, while in other embodiments, the virus comprises an Ann Arbor B strain influenza backbone, a B/Leningrad/14/17/55 backbone, a B/14/5/1, a B/USSR/60/69 backbone, a B/Leningrad/179/86 backbone, a B/Leningrad/14/55 backbone, or a B/England/2608/76 backbone. In some embodiments, the virus is ca B/Jilin/20/03. In certain embodiments, the eggs are SPF hen eggs. In some embodiments, the host cells are MDCK cells. Also, in certain embodiments, the incubation below 33° C. comprises incubating the eggs or other host cells (e.g., MDCK and Vero) at between 29° C. and 33° C., or between 31° C. and 33° C., or between 31° C. and 32° C., or at 31° C.

In other aspects the invention comprises influenza virus produced by such methods above, as well as compositions comprising such viruses and influenza vaccine comprising such viruses (e.g., liquid live attenuated intranasal vaccines). Such virus that can be grown through the current invention, can optionally comprise, e.g., CAIV (cold-adapted influenza viruses, e.g., in trivalent formulations), viruses such as those in PCT Publication WO 05/014862, viruses such as those described in, e.g., PCT Publications WO 01/183794, WO 00/60050, U.S. Pat. Nos. 6,544,785 and 6,649,372 as well as other similar and related viruses and virus types.

These and other objects and features of the invention will become more fully apparent when the following detailed description is read in conjunction with the accompanying figures and claims.

BRIEF DESCRIPTION OF THE DRAWINGS

FIG. 1: Displays a table showing virus yield (TCID$_{50}$/mL) of ca B strains as a function of secondary incubation temperature.

FIG. 4: Displays a table with phenotypes of various ca influenza B strains expressing the characteristic ca and ts phenotypes when grown in eggs incubated at temperatures between 29° C. and 33° C.

FIG. 5: Displays a table showing HA titer of allantoic fluids from infected eggs incubated at various temperatures and harvested 72 hours after infection.

FIG. 6: Displays a table showing the quantity of HA viral RNA in the allantoic fluid of infected eggs incubated at various temperatures.

FIG. 7: Displays a table showing the ratio of genome copy to infectious virus determined by subtracting the quantity of infectious particles (log$_{10}$ TCID$_{50}$) from the copy number.

FIG. 8: Displays a table showing percent infectious particles of ca B/Jilin/20/03 and ca B/Ann Arbor/1/94 when grown at 31 and 33° C.

FIG. 9: Displays a table showing nucleotide sequences of ca B/Jilin/20/03 grown at 33° C. (1 Lot) and 31° C. (2 Lots) as compared to the corresponding MVS.

FIG. 10: Displays a table comparing HAI titers of viruses grown at two temperatures with respect to antisera produced against wt B/Jilin/20/03.

FIG. 12: Displays a table comparing HAI titer of sera at day 14 from ferrets immunized with ca B/Jilin/20/03 grown at either 31 or 33° C.

DETAILED DESCRIPTION

Figure 2:
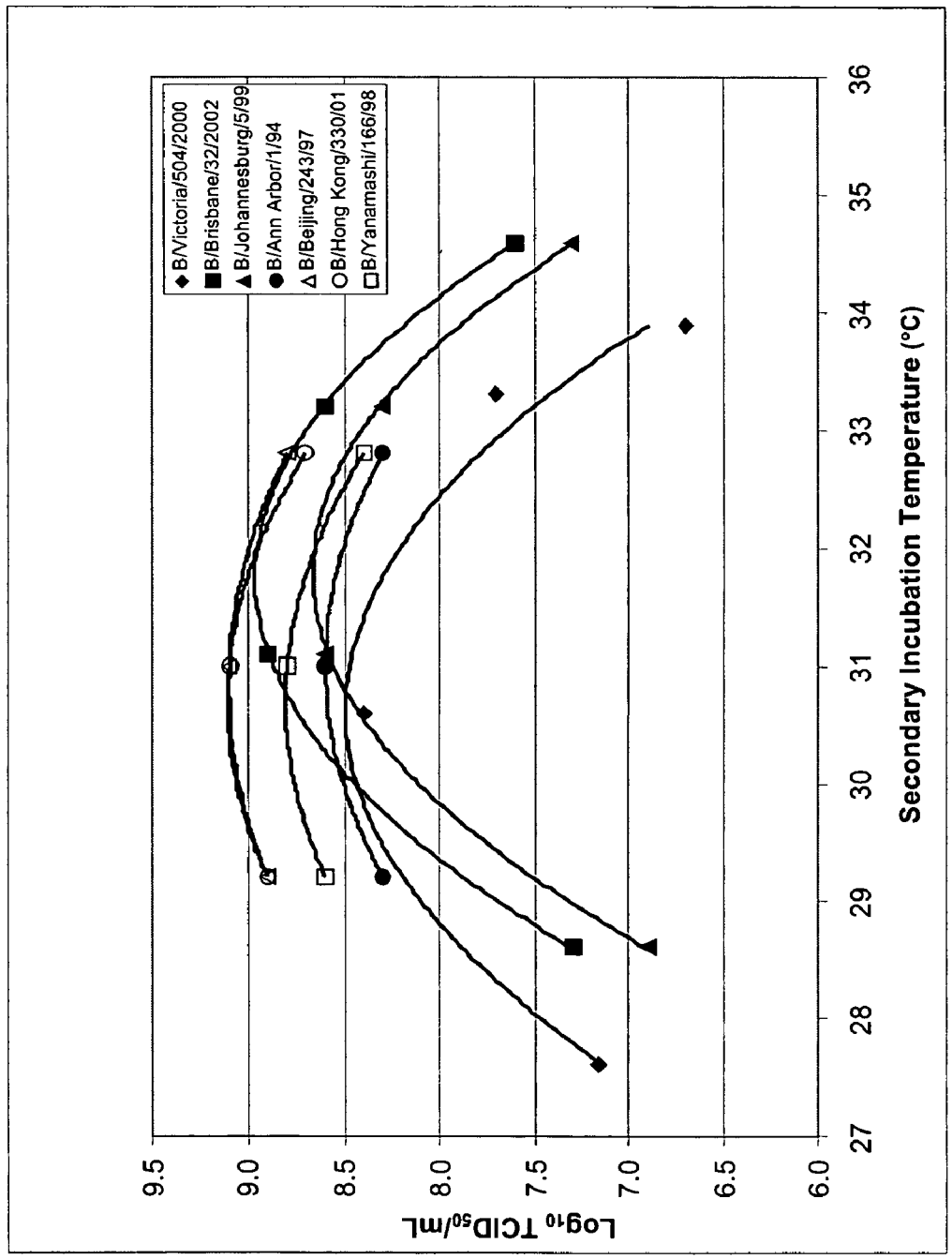
FIG. 2: Shows the a graph of the yield (TCID$_{50}$/mL) of ca B strains as a function of the secondary incubation temperature.

The present invention includes methods for increased production of virus, more specifically cold-adapted influenza B virus strains, that are suitable for the production of vaccines, including, but not limited to FluMist®. Included are methods for, e.g., growth of viral strains at lowered temperatures during incubation in eggs, (e.g., secondary incubation in eggs) or other host cells (e.g., MDCK and Vero) after inoculation. Additional features as described in more detail herein.

It will be appreciated by those skilled in the art that typical embodiments herein also comprise steps/methods/compositions that are known in the art, e.g., candling of eggs, inoculation of eggs with viruses, etc. Therefore, those skilled in the art are able to determine appropriate conditions, sub-steps, step details, etc., for such known steps to produce the appropriate viruses, virus solutions, compositions. The individual steps are described in greater detail below.

It will also be appreciated by those skilled in the art that the various steps herein for virus/vaccine production are not required to be all performed or exist in the same production series. Thus, while in some embodiments, all steps and/or compositions described or mentioned herein are performed or exist, in other embodiments, one or more steps are optionally, e.g., omitted, changed (in scope, order, placement, etc.) or the like.

Production of Cold-Adapted Influenza B Strains

The overall yield of certain cold-adapted (ca) influenza B strains, such as the B/Jilin/20/03 strain, which are intended for use in vaccine formulation is sometimes insufficient to enable adequate production of a desired number of influenza vaccine doses when grown following the currently approved manufacturing conditions of secondary incubation at 33° C. The current invention includes methods for incubation of eggs or other host cells (e.g., MDCK and Vero) at temperatures of less than 33° C., e.g., 31° C. (or optionally at between about 29° C. and about 32° C.), rather than 33° C., which increases the yield of such strains and thus allows the increased production of the virus for vaccine. Such egg or other host cells (e.g., MDCK and Vero) incubations are optionally described as "secondary" incubations herein to differentiate them from primary incubations of eggs at 37° C. used to develop the embryos of the eggs or of host cells at higher temperatures used to proliferate the cells prior to infection. Examples herein compare the characteristics of the B/Jilin/20/03 strain, and other ca influenza B strains, grown at 31° C. and 33° C. and show that virus grown at 31° C. share indistinguishable biological characteristics as virus grown at 33° C.

The data included in the examples herein demonstrate that the higher yield of ca B/Jilin/20/03 at temperatures below 33° C. (e.g., 31° C.) is not unique to the B/Jilin/20/03 strain. All other ca influenza B strains tested also replicated more efficiently at temperatures below 33° C., including ca B/Ann Arbor/1/94, which has shown demonstrable efficacy in pivotal trials of vaccine. In addition, the examples herein show detailed characterization of ca B/Jilin/20/03 vaccine from viruses grown at 31° C. and at 33° C. which emphasizes that the two vaccines are equivalent to each other in the characteristics examined. Indeed, the physical and biological characteristics of ca B virus vaccine strains grown at temperatures below 33° C., e.g., 31° C., are equivalent to those of other ca influenza B strains grown at 33° C. that have been used or tested in humans. See below.

The results of the comparability and characterizations described in the examples herein show that growth curves of ca B/Jilin/20/03 and seven other ca influenza B strains in eggs all yielded higher titers of virus when grown at temperatures below 33° C. (with optimal temperatures generally between 29° C. and 32° C.). Also, growth at lower temperatures did not adversely change the hallmark biological traits of the vaccine. Thus, the different ca influenza B vaccine strains, including ca B/Jilin/20/03, expressed the characteristic ca and temperature sensitive (ts) phenotypes whether originally grown at 29° C., 31° C., or 33° C. Furthermore, the overall ratio of total particles to infectious particles was similar among the different strains, including ca B/Jilin/20/03, and was equivalent between 31° C. and 33° C. The quantity of total particles was measured by determining the genome copy number by quantitative RT-PCR. In addition, ca B/Jilin/20/03 total particles were also measured by transmission electron microscopy. The examples herein, also show that the genomes of ca B/Jilin/20/03 grown at 31° C. or 33° C., when sequenced, are identical to each other as well as to the master virus seed (MVS) and that the antigenicity of ca B/Jilin/20/03 grown at 31° C. or 33° C. is substantially the same, as shown by hemagglutination-inhibition assay (HAI). The examples herein also demonstrate that replication in eggs of ca B/Jilin/20/03 grown at 31° C. or 33° C. is equivalent with respect to time and optimum temperatures and that replication in the nasopharynx of ferrets of ca B/Jilin/20/03 grown at 31° C. or 33° C. is also equivalent. Furthermore as shown by the examples herein, the immunogenicity of ca B/Jilin/20/03 is equivalent whether grown at 31° C. or 33° C. For example, groups of ferrets were immunized with these two preparations and the HAI titers of the animals measured 14 days post immunization. The mean HAI titers of the sera from these two groups of animals were identical.

Such combined data demonstrates that the biological characteristics of ca B/Jilin/20/03 are comparable whether the virus is grown at temperatures below 33° C. (e.g., 31° C.) or at 33° C. The vaccine strains have equivalent biophysical characteristics (e.g., antigenicity, total particle to infectious particle ratios and sequence) as well as biological properties both in vitro and in vivo. Additionally, the better growth of ca B/Jilin/20/03 at temperatures below 33° C. (e.g., 31° C.) also applies to other ca influenza B strains. Thus, the current invention includes growth of such virus strains, e.g., ca B/Jilin/20/03 strain, or other ca influenza b strains, at temperatures below 33° C. (e.g., 31° C.) for such uses as manufacturing of vaccines such as FluMist®, etc.

Thus, in certain embodiments, the invention comprises a method of producing influenza virus particles by introducing at least one vector (e.g., a B strain influenza virus such as a 6:2 reassortant virus that can optionally comprise PR8, Ann Arbor B strain influenza, B/Leningrad/14/17/55, B/14/5/1, B/USSR/60/69, B/Leningrad/179/86, B/Leningrad/14/55, B/England/2608/76, or ca B/Jilin/20/03, or one or more plasmids) comprising a genome, or partial genome (e.g., comprising one, two, three, four, five, six, or seven (i.e., less than all vRNA segments) vRNA segments) of an influenza virus, into at least one host egg or other host cells (e.g., MDCK and Vero) capable of supporting replication of influenza virus; incubating the host egg or other host cells (e.g., MDCK and Vero) at a temperature below 33° C.; and, recovering the influenza virus particle, from the host egg or other host cells (e.g., MDCK and Vero). In other embodiments, the invention provides a method of increasing the yield of influenza virus particles comprising incubating said virus particles at a temperature below 33° C. (e.g., 31° C.). In a specific embodiment, the invention comprises a method of increasing the yield of influenza virus particles by introducing at least one vector comprising a genome or partial genome of an influenza virus into at least one host egg or other host cells (e.g., MDCK and Vero); incubating the host egg or other host cell at a temperature below 33° C.; wherein the yield of influenza virus particles produced at a temperature below 33° C. is greater than that of the same virus particles produced at 33° C. In certain embodiments the $\log_{10}$ TCID$_{50}$/mL titer of virus particles produced at a temperature below 33° C. is greater than that of the same virus particles produced at 33° C. In certain embodiments, the $\log_{10}$ TCID$_{50}$/mL titer of a virus produced at a temperature of less then 33° C. is at least about 7.0, or at least about 7.2, or at least about 7.4, or at least about 7.6, or at least about 7.8, or at least about 8.0, or at least about 8.2, or at least about 8.4, or at least about 8.6, or at least about 8.8, or at least about 9.0, or at least about 9.2, or at least about 9.4, or at least about 9.6, or at least about 9.8. In other embodiments, the methods of the present invention include introducing influenza virus (e.g., a reassortant virus) into one or more embryonated eggs that are capable of supporting replication of influenza virus, thereby infecting said embryonated eggs. In still other embodiments, the methods of the present invention include introducing influenza virus (e.g., a reassortant virus) into host cells (e.g., MDCK and Vero) that are capable of supporting replication of influenza virus, thereby infecting said host cells. The virus involved can optionally comprise: an attenuated influenza virus, a cold adapted influenza virus, a temperature sensitive influenza virus, an attenuated cold adapted temperature sensitive influenza virus; or any combination thereof. It is contemplated that the virus involved is a 6:2 reassortant virus. In one embodiment, the virus involved is a B strain influenza virus 6:2 reassortant. B strain influenza viruses which may be utilized in the methods of the present invention include, but are not limited to, PR8, Ann Arbor B strain influenza (e.g., B/Ann Arbor/1/94, B/Ann Arbor/1/66), B/Leningrad/14/17/55, B/14/5/1, B/USSR/60/69, B/Leningrad/179/86, B/Leningrad/14/55, B/England/2608/76, or ca B/Jilin/20/03. In another embodiment, the virus involved comprises at least one segment of an Ann Arbor B strain influenza or a B virus selected from the group: B/Leningrad/14/17/55, B/14/5/1, B/USSR/60/69, B/Leningrad/179/86, B/Leningrad/14/55, B/England/2608/76, and ca B/Jilin/20/03.

In certain aspects, the host egg is an SPF embryonated hen egg. In certain other aspects, the host cell is an animal cell. Animal cells useful for the production of influenza virus are known in the art and include, but are not limited to, MDCK cells (see, for example, U.S. Pat. Nos. 4,500,413 and 6,455,298), Vero cells (see, for example, U.S. Pat. No. 6,146,873) and PerC6 cells (see, for example, PCT Publications WO 01/38362 and WO 02/40665). In one embodiment, the host cell is an MDCK cell. Also, in certain aspects, the incubating occurs at between about 29° C. and about 33° C., between about 31° C. and about 33° C., or at between about 31° C. and about 32° C., or at about 31° C. In other aspects, the incubating occurs at between 29° C. and 33° C., between 31° C. and 33° C., or at between 31° C. and 32° C., or at 31° C. The invention also encompasses an influenza virus produced by the methods herein and compositions and vaccines comprising such virus (e.g., liquid live attenuated intranasal vaccines such as FluMist).

In particular aspects, the methods herein comprise embodiments wherein the titer ($\log_{10}$ TCID$_{50}$/mL) that results from incubating the eggs or other host cells (e.g., MDCK and Vero) below 33° C. is greater than or equal to a titer that results from incubating the same virus particle (i.e., the same virus type/strain, etc.) at 33° C. or higher. Such comparison is optionally done between incubations at 31° C. and incubations at 33° C. In various embodiments, the $\log_{10}$ TCID$_{50}$/mL titer resulting from the incubation at 31° C. is from at least about 1.01 to at least about 1.10 times greater, from at least about 1.025 to at least about 1.05 greater, or from at least about 1.03 to at least about 1.04 times greater, than the $\log_{10}$ TCID$_{50}$/mL titer resulting from incubation at 33° C. In other embodiments, the $\log_{10}$ TCID$_{50}$/mL titer resulting from the incubation at 31° C. is from at least 1.01 to at least 1.10 times greater, from at least 1.025 to at least 1.05 greater, or from at least 1.03 to at least 1.04 times greater, than the $\log_{10}$ TCID$_{50}$/mL titer resulting from incubation at 33° C.

In yet other aspects, the methods herein comprise embodiments wherein the ca and/or ts phenotype of the virus particle is essentially similar when the virus is incubated below 33° C. (e.g., 31° C.) or at 33° C. or above (e.g., at 33° C.). Also, in particular aspects, the methods herein comprise embodiments wherein the viral yield of the virus particle resulting from incubation below 33° C. (e.g., 31° C.) is greater than or equal to viral yield of the same virus particle when incubated at 33° C. (e.g., at 33° C.) or higher. In such aspects, the viral yield is optionally quantified through the use of a median tissue culture infectious dose (TCID$_{50}$) assay that measures infectious virions of the allantoic fluid of the host eggs infected with the virus particle that are incubated at below 33° C. and a median tissue culture infectious dose (TCID$_{50}$) assay that measures infectious virions of the allantoic fluid of the host eggs infected with the virus particle that are incubated at 33° C. or above. Alternatively, the viral yield is optionally quantified through use of a hemagglutination titer of the allantoic fluid of the host eggs infected with the virus particle that are incubated at below 33° C. and a hemagglutination titer of allantoic fluid of the host eggs that are infected with the virus particle and incubated at 33° C. or above. The viral yield is also optionally quantified by comparison of the quantity of viral RNA in the allantoic fluid of the host eggs infected with the virus particle incubated at below 33° C. and the quantity of viral RNA in the allantoic fluid of the host eggs infected with the virus particle incubated at 33° C. or above. The viral yield is also optionally quantified by comparison of the percent infectious particles in the allantoic fluid of the host eggs that are infected with the virus particle and incubated at below 33° C. and the percent infectious particles in the allantoic fluid of the host eggs that are infected with the virus particle and incubated at 33° C. or above. The viral yield is optionally quantified through the use of a median tissue culture infectious dose (TCID$_{50}$) assay that measures infectious virions of the allantoic fluid of the supernatant of the host cells infected with the virus particle that are incubated at below 33° C. and a median tissue culture infectious dose (TCID$_{50}$) assay that measures infectious virions of the supernatant of the host cells infected with the virus particle that are incubated at 33° C. or above. Alternatively, the viral yield is optionally quantified through use of a hemagglutination titer of the supernatant of the host cells infected with the virus particle that are incubated at below 33° C. and a hemagglutination titer of the supernatant of the host cells infected with the virus particle that are incubated at 33° C. or above. The viral yield is also optionally quantified by comparison of the quantity of viral RNA in the supernatant of the host cells infected with the virus particle incubated at below 33° C. and the quantity of viral RNA in the supernatant of the host cells infected with the virus particle incubated at 33° C. or above. The viral yield is also optionally quantified by comparison of the percent infectious particles in the supernatant of the host cells that are infected with the virus particle and incubated at below 33° C. and the percent infectious particles in the supernatant of the host cells that are infected with the virus particle and incubated at 33° C. or above.

In certain other aspects, the methods of the invention include wherein a nucleic acid sequence of the infectious viral particle incubated at below 33° C. is identical to a nucleic acid sequence of the infectious virus particle when incubated at 33° C. or above. In certain other aspects, the methods of the invention include wherein antigenicity of the virus particles that are incubated at below 33° C. is substantially the same as the antigenicity of the same virus particles (i.e., same virus type, etc.) when they are incubated at 33° C. or above. Such antigenicity is optionally measured by HAI assay. In yet other certain aspects, the methods of the invention include wherein the virus particles provoke an immune response in a subject (e.g., a ferret, a human, a non-human primate, a mammal), that is essentially the same as, or similar to, an immune response provoked in the same subject (or subject type) by a virus particle of the same type produced through incubation at 33° C. or above.

EXAMPLES

Characterization/Comparison of B/Jilin/20/03 and Other B Viruses Grown at 31° C. and 33° C.

Growth Curves of ca B/Jilin/20/03 and Other ca Influenza B Strains

Figure 3:
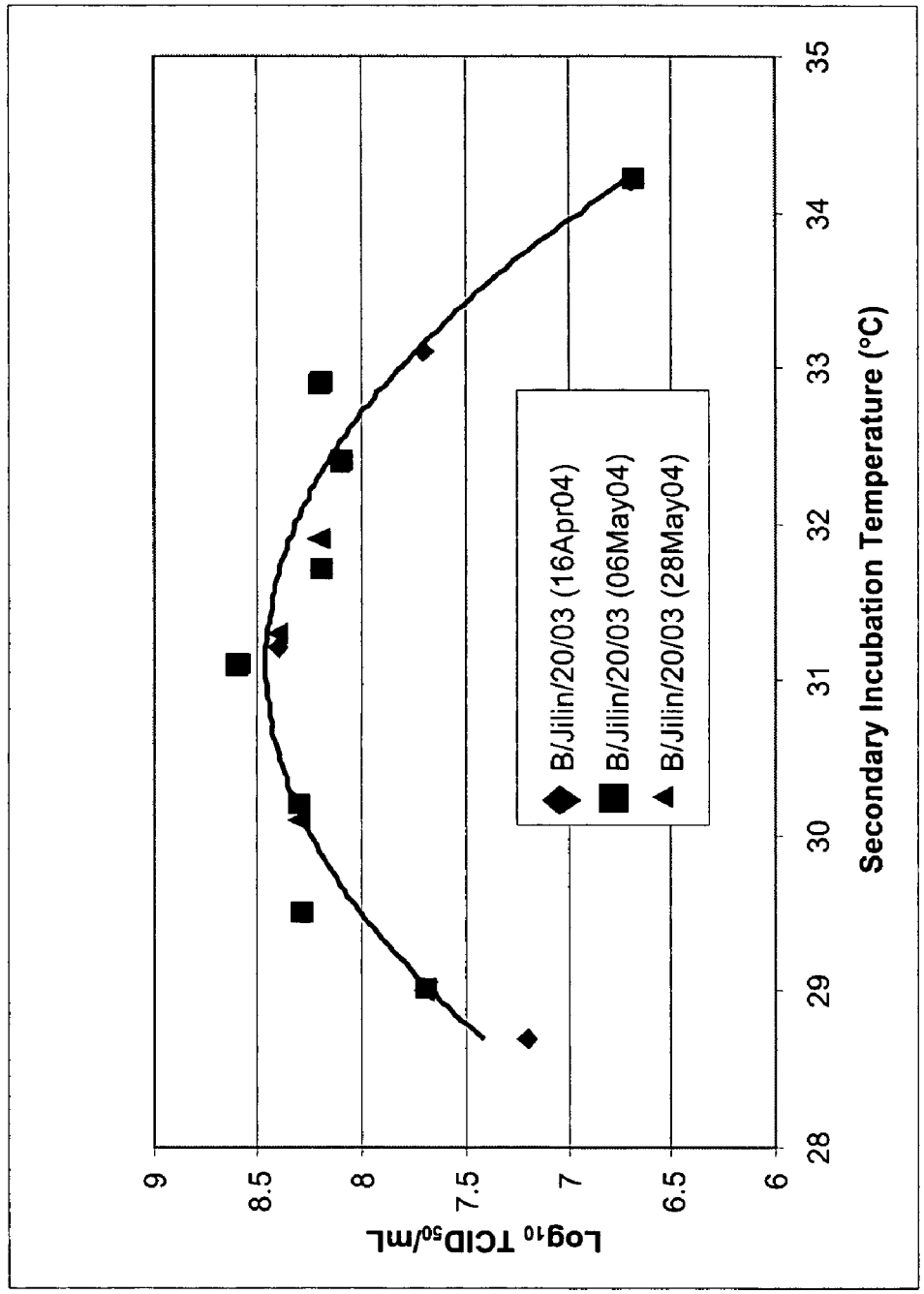
FIG. 3: Displays a table showing virus yield (TCID$_{50}$/mL) of ca B/Jilin/20/03 as a function of the secondary incubation temperature.

As seen in the current examples, the optimal yield of ca influenza B strains was highest following incubation of embryonated specific pathogen free (SPF) hen eggs between 30° C. and 32° C. Embryonated SPF eggs were inoculated with a variety of different ca influenza B strains at approximately 2.1 log$_{10}$TCID$_{50}$/egg and incubated at temperatures ranging from 28° C. to 35° C. for 60-72 hours. After incubation, the allantoic fluids of the infected eggs were harvested and titered. As shown in the table in FIG. 1 and the graph in FIG. 2, the optimal temperature of incubation was below 33° C. and was typically between 31° C. and 32° C. As can be seen, the temperature profiles were similar for all strains tested, including ca B/Ann Arbor/1/94 which had significant clinical efficacy against wt influenza B (see, e.g., Belshe, et al., *Phil. Trans. R. Soc. Lond. B,* 2001, 356:1947-1951, and Belshe, et al., *Pediatrics,* 2001, 108:24+) and ca B/Jilin/20/03 which is a strain of particular significance in recent influenza seasons. See FIGS. 2 and 3.

The optimal temperature of incubation for each strain was determined by interpolation of the best-fit polynomial line through the data points for each strain. Seven ca influenza B strains including representatives of both the Yamagata lineage (B/Ann Arbor/1/94, B/Victoria/504/2000, and B/Johannesburg/5/99) and Victoria lineage (B/Yamanashi/166/98, B/Brisbane/32/2002 and B/Beijing/243/97) were incubated at various temperatures and harvested between 60 and 72 hours post infection. The optimal temperature was below 33° C. and typically between 31° C. and 32° C. See FIG. 2. Three independent replicates of the temperature profile of ca B/Jilin/20/03 are displayed in FIG. 3. As can be seen, an optimal temperature of incubation for ca B/Jilin/20/03 was approximately 31° C.

Cold-Adaptation (ca) and Temperature Sensitivity (ts) Phenotype Assay—Ratio of Virus Titers at 25° C., 33° C., and 37° C. on Primary Chick Kidney Cells Cold-Adapted influenza B strains grown in embryonated SPF eggs between 29° C. and 33° C. were shown to express the characteristic ca and ts phenotypes. In order to demonstrate that the incubation conditions would have no impact on the biological properties of a resulting vaccine, materials grown at various temperatures were evaluated for the presence of the characteristic ca and ts phenotypes. All strains exhibited these characteristic traits, thus, indicating that the incubation temperature of the eggs would have no impact on the vaccine strains. See FIG. 4.

Measurements of Viral Yield Via Hemagglutination (HA) Titer, Quantity of Viral RNA, and Percent Infectious Particles Other measurements of viral yield are consistent with the yield of infectious virus. Samples of virus harvested at various temperatures were assayed for HA activity and the amount of viral RNA was quantified by quantitative reverse transcribed PCR (QRT-PCR). The results shown in FIGS. 5 and 6 were consistent with the TCID$_{50}$ results. The highest HA activity and vRNA quantity were observed with eggs that had been incubated at 31° C.

The quantity of the HA gene segment viral RNA in the allantoic fluid of infected eggs incubated at various temperatures and harvested 72 hours after infection is provided in FIG. 6.

The ratio of total particles, measured by either genome copy number or transmission electron microscopy (TEM), to infectious particles is also evaluated in the examples herein. The ratio of copy number to $TCID_{50}$ (FIG. 7) revealed that there is a constant ratio of gene copy number to $TCID_{50}$ between samples incubated at either 31° C. or 33° C.

In the examples, the TEM was used to evaluate the ratio of the virus particles to the $TCID_{50}$ for selected samples. Similar to the genome:$TCID_{50}$ ratios, this analysis demonstrated that approximately 3.3% of the total particles of B/Jilin/20/03 grown at 31° C. were infectious. See FIG. 8. The percentage of infectious particles for B/Jilin/20/03 grown at 31° C. is comparable to the value obtained at 33° C. and is also similar to values obtained for B/AnnArbor/01/94 grown at either 31 or 33° C. These ratios are also within the range of those for other ca influenza B vaccine strains reported earlier Genomic Sequence Analysis of B/Jilin/20/03 Viruses Grown at 31° C. or 33° C.

As shown in the examples herein, viral RNAs (vRNAs) were extracted from virus grown at 31° C. and 33° C. and sequenced. The genomic sequences of these viruses grown at different temperatures are identical to each other and the MVS. See FIG. 9.

Anti Genicity as Shown by HAI of ca B/Jilin/20/03 Grown at 31° C. or 33° C.

The viruses in the examples were tested to determine whether their antigenic characteristics were comparable. The HAI titers of ca B/Jilin/20/03 grown at 31° C. and 33° C. were evaluated with respect to reference B/Jilin/20/03 antisera. The HAI titers were within 2-fold of each other, demonstrating their antigenicity is identical. See FIG. 10.

In Vivo Characteristics of Virus Grown at 31° C. or 33° C.

Figure 11:
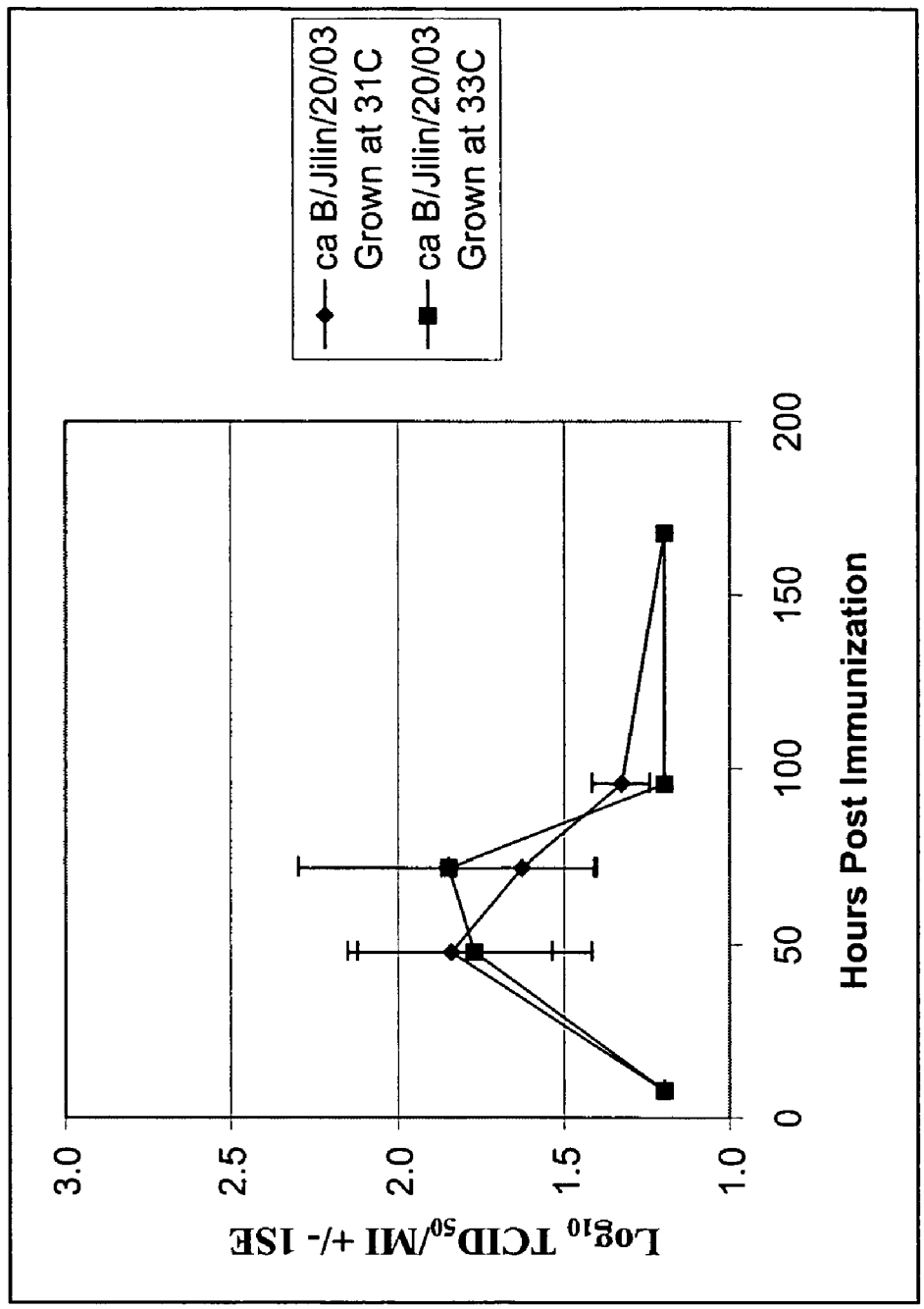
FIG. 11: Shows a graph illustrating virus replication in ferrets after intranasal inoculation with ca B/Jilin/20/03 virus grown at either 31 or 33° C.

In order to evaluate the performance of the vaccine grown at these two temperatures, groups of five ferrets (seronegative) were inoculated intranasally with 7.0 $\log_{10}$ $TCID_{50}$ of virus grown at either 31° C. or 33° C. The replication of the vaccine in the nasopharynx of these animals was determined by measuring the viral titer in nasal wash specimens at various time points after immunization. Vaccine virus replication was equivalent in both quantity and duration between the two groups. See FIG. 11. In addition, the animals were bled 14 days after immunization and the titers of antibody in the sera to wt B/Jilin/20/03 were determined by HAI. The antibody responses to immunization were identical between these two groups of animals, thus, demonstrating that the vaccine is equally immunogenic whether it was grown at 31° C. or 33° C. See FIG. 11.

Figure 13:
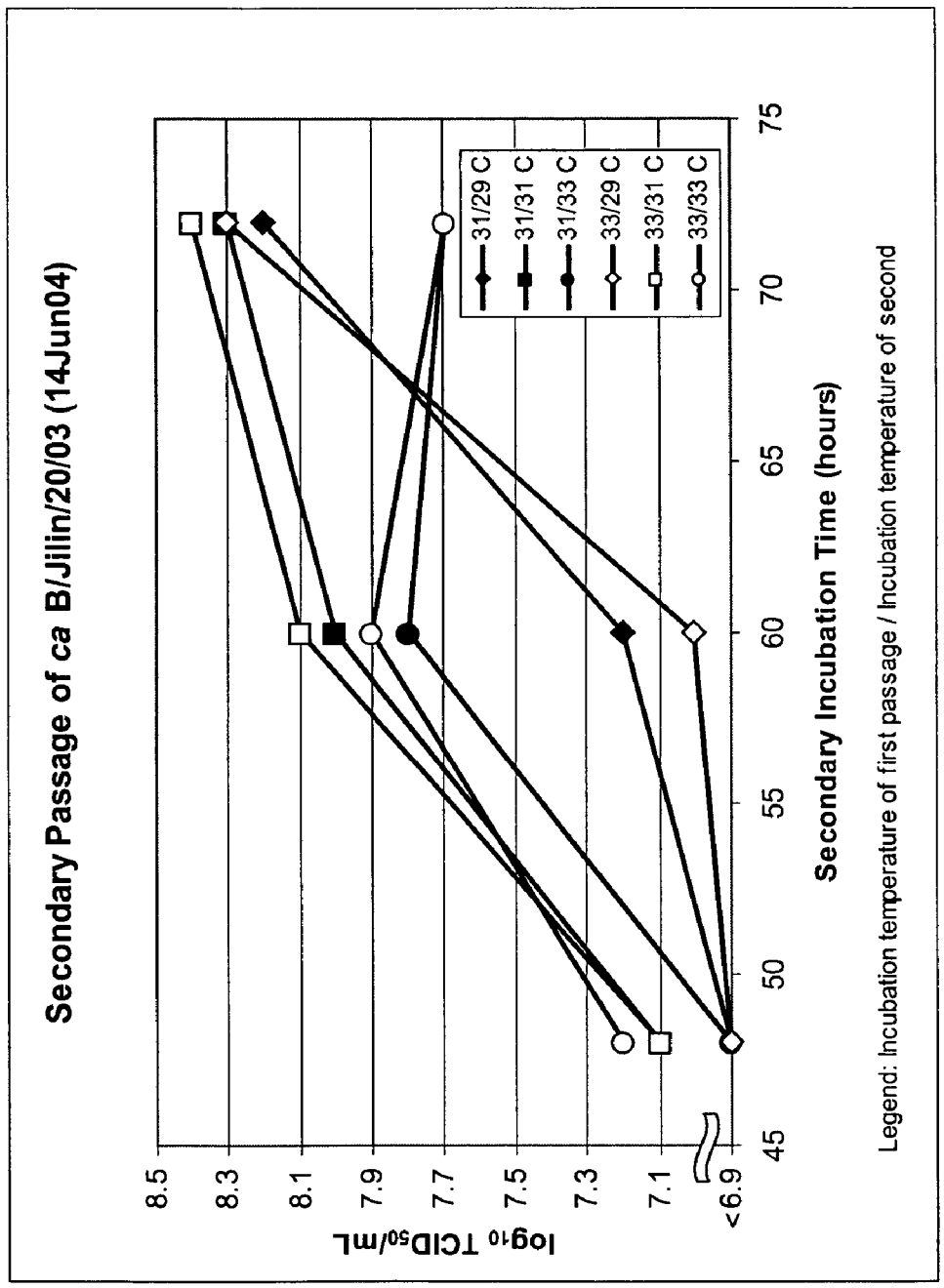
FIG. 13: Shows a graph illustrating secondary passage of 31 and 33° C. grown ca B/Jilin/20/03 in SPF eggs at different secondary incubation temperatures.

In order to demonstrate that growing ca B/Jilin/20/03 at 31° C. had no impact on its ability to grow at temperatures similar to those found in the human nasopharynx, vaccine grown at both 31° C. and 33° C. were inoculated into SPF eggs and incubated at temperatures between 30° C. and 33° C. As shown in FIG. 13, both vaccines replicated with equivalent temperature profiles with both yielding the highest titers at approximately 31° C. (the temperature expected to be found in the human upper airways).

The data presented in the examples herein, demonstrate that the biological and biophysical characteristics of ca B/Jilin/20/03 are comparable when grown at either 31° C. or 33° C. The vaccine strain grown at these two temperatures has equivalent biophysical characteristics (antigenicity, total particle to infectious particle ratios and sequence) as well as biological properties both in vitro and in vivo, including expression of the ca and ts phenotypes, replication and immunogenicity in animals, and replication in eggs at different temperatures. However, the virus grown at 31° C., as opposed to 33° C., showed a higher production of virus. Additionally, the better growth of ca B/Jilin/20/03 at 31° C. is also shown herein for other ca influenza B strains tested. Thus, the examples herein support the claims of the current invention in growing the ca B/Jilin/20/03 strain (and other ca influenza B strains) at temperatures of less than 33° C., e.g., 31° C. (or optionally at between about 29° C. and about 32° C.), rather than 33° C., in eggs or other host cells (e.g., MDCK and Vero), e.g., for use in manufacturing of vaccines such as FluMist® or other vaccines.

EXAMPLES

Materials and Methods

Phenotype Assays—ca and ts

Phenotype assays were performed on primary chick kidneys (PCK) cells prepared from 3-day-old chicks. The samples were assayed for ca and ts phenotype. Briefly, PCK cells were washed with serum free medium (PAM) and used in titration of the samples. The washed cell layers were inoculated with the appropriate virus and incubated at the indicated temperatures. The cell layers were then examined for cytopathic effect on the cells caused by the replicating virus resulting in dead cells. Phenotypes were assigned as: ca—the $TCID_{50}$ average titer difference between 33° C. and 25° C. was two logs or less; and, ts—the $TCID_{50}$ average titer difference between 37° C. or 39° C. and 33° C. was two logs or more. The samples were tested in duplicate at 25° C., 33° C., and 37° C. The plates were incubated for six days (ts phenotype) or ten days (ca phenotype) and CPE readings were taken at the end of incubation. The titers reported in the examples herein were an average $TCID_{50}$/mL±SD.

HA and HAI Assays

Hemagglutination (HA) assay was performed using 0.5% chick RBCs prepared in PBS. The samples were serially two-fold diluted in 96 well plates in a 50 µL volume. To the serially diluted sample, 50 µL of 0.5% chick RBCs were added and mixed and the plates were incubated for a minimum of 30 minutes before being read for HA activity. Each sample was tested in duplicate and the HA titer was reported as an average of two replicates.

In the HAI assay, serum samples were treated and two-fold serially diluted starting at 1:4 dilution in a 25 µL volume. Twenty-five microliters of virus, corresponding to 4 HA units, were added and mixed, and the sample was incubated for a half-hour at room temperature. At the end of the incubation, 50 µL of 0.5% chick RBCs were added and mixed and the plates were incubated for a minimum of 30 minutes before they were read for HAI activity.

Replication and Immunogenicity in Ferrets

Ferrets (7 week old) were obtained and quarantined in a controlled facility for 2 weeks. A volume of inoculum sufficient to administer 1 mL to each of five ferrets was freshly prepared by diluting influenza virus stocks to a final dose of 7.05 $\log_{10}$ $TCID_{50}$ in 1×SPG.

The animals were bled to obtain a pre-immunization serum sample, and then immunized intranasally with 1 mL (0.5 ml per nostril) of ca B/Jilin/20/03 that had been grown at either 31° C. or 33° C. Following inoculation, nasal samples were collected from each ferret at specified intervals from 8 to 168 hours post immunization by washing the nasal passages with 1 mL sterile phosphate-buffered saline. Recovered nasal wash samples were immediately frozen and stored at −80° C. until they were used for viral titration. Serum was collected at days 0, 14, 21 and 28 for determination of HAI response.

To measure the titer of virus in the nasal wash samples, MDCK cells were seeded into 96-well flat-bottom tissue culture plates and grown to 100% confluency at 37° C. and 5% $CO_2$. Immediately prior to assaying nasal wash samples, cell growth media was removed from each well, the cells were washed twice with incomplete viral growth media (VGM) without TPCK-trypsin, and then with complete VGM (0.18 mL), TPCK-trypsin was added to every well. At the same time, nasal wash samples were thawed and serially diluted in complete VGM. Aliquots (0.02 mL) of diluted virus or media only (negative control) were then added to eight wells each on triplicate plates. Plates were placed at 33° C. and 5% $CO_2$ for six days and then scored microscopically for the presence of viral cytopathic effect (CPE) in every well. The number of CPE-positive wells per plate was converted into a median infectious dose ($TCID_{50}$/mL) value using the Karber method.

Replication in Eggs

In order to produce the virus-containing allantoic fluids for the different ca B strains, specific pathogen-free (SPF) eggs were stored for less than 7 days at 14±2° C. following receipt and were incubated at 37.5±1° C. and 70±10% relative humidity for 264±12 hours. After incubation, the eggs were removed, candled and acceptable eggs inoculated with approximately 2.1 $\log_{10}$ $TCID_{50}$/egg of virus and incubated at temperatures ranging from 28° C. to 35° C. for 48, 60 72 or 84 hours. The eggs were then candled and chilled at 5±3° C. for 12-24 hours prior to harvesting. The eggs were surface sanitized by spraying with 70% v/v ethanol and transferred to a bio-safety cabinet (BSC) and allowed to air dry. The eggs in the BSC were prepared for harvesting by punching the top of the egg using an egg puncher. The punched eggshells were removed using a sterile stainless steel spatula and the allantoic fluid subsequently harvested using a 10 mL pipette. The harvested allantoic fluid from each harvest time point was collected and samples aliquoted and stored at or below −60° C. prior to titration.

$TCID_{50}$ Assay

The $TCID_{50}$ assay was performed according to the following method. Of course, it will be appreciated that other similar assays could also be used. 96-well plates of 4-day old and 100% confluent Madin Darby Canine Kidney (MDCK) cells were used for the assay. The cell culture plates were washed 2 times with virus growth medium (VGM) using a Skatron™ Cell Washer. 180 µl per well of complete VGM with trypsin were added to each plate and the plates were placed in 33° C. and 5% CO2 until inoculation. At the same time, the test virus and control virus samples were thawed and prediluted in VGM with trypsin in 96-well pre-dilution blocks. The samples were serially 10-fold diluted to 10-3 to 10-4 using a SerialMate pipetting station. The virus samples were then transferred from the pre-dilution blocks to the 1st and 12th columns of freshly prepared dilution blocks filled with VGM with trypsin. The samples were further serially diluted by SerilMate pipetting station to 10-5 to 10-10. The MDCK cell culture plates containing VGM with trypsin were removed from the incubator and inoculated with the diluted virus samples using SerialMate pipetting station. The plates were placed in 33° C. and 5% CO2 for six days. Methylthiazole-tetrazolium (MTT) dye was added to the tissue culture plates to detect the cytopathic effect (CPE). The plates were then read with a spectrophotometer to determine the number of CPE wells in the tissue culture plates. The $TCID_{50}$ titer of the samples was calculated based on the total number CPE wells.

Sequence Analysis

Three viral materials were analyzed by sequencing. Two viral expansions, Z0015 PD 16 Apr. 2004, DQ NB 773 and Z0015 PD 16 Apr. 2004, DQ NB 773, were grown at 33° C. and 31° C., respectively. Manufacturer's Lot, Batch No. 600054C, grown at 31° C., was also included in the study. As reference, B/Jilin/20/03 MVS, Lot No. 0141900073, was used.

For sequencing, viral RNA was isolated using QIAamp Viral RNA Mini Kit (Qiagen, Venlo, The Netherlands), and cDNA was amplified by RT-PCR as template. Sequence reactions were carried out using ABI PRISM™ BigDye Terminator Cycle Sequencing Ready Reaction Kit (Applied Biosystems, Foster City, Calif.) with a set of specific sequence primers and each amplified cDNA template, following the manufacturer's instructions. Sequence extension products were purified and analyzed by capillary electrophoresis using ABI Genetic Analyzer 3730 (Applied Biosystems, Foster City, Calif.). Sequence results were analyzed using DNA Sequencing Analysis (Applied Biosystems) and Sequencer (Gene Codes Corp.).

Q RT-PCR for Genome Copy Number Determinations

To determine the genome copy number, RNA was extracted in duplicate or triplicate using the Qiagen QIAamp Viral RNA mini kit. RNA was reverse transcribed in duplicate using the High Capacity cDNA Archive Kit (Applied Biosystems, Foster City, Calif.). The cDNAs were analyzed singly by Q-PCR using primers and a probe specific for the HA gene of Influenza B virus using the TaqMan Universal Master Mix (Applied Biosystems) on the ABI Prism 7700 Sequence Detection System (Applied Biosystems). Results were analyzed using Sequence Detection Software, Version 1.9 (Applied Biosystems) and values converted to copies/mL in Microsoft Excel.

Viral RNA quantity was determined with the use of a standard curve generated with serial dilutions of a plasmid containing the B/Yamanashi HA gene. Plasmid was diluted from 10 pg down to 1 fg per reaction. Quantity per reaction was converted to virus/mL by multiplying the fg HA RNA/reaction×4,000,000 (virus diluted 1:10 pre-extraction, RNA diluted 1:10 during the RT step, 5 μL of cDNA analyzed with approximately 200 molecules of viral RNA per fg HA plasmid). These calculations assume 100% efficiency of all steps and that there is no extra-viral RNA present.

Total Particle Count Using Transmission Electron Microscopy

Total particle count determinations by transmission electron microscopy were performed by Advanced Biotechnologies, Inc., Columbia, Md. Each preparation was vortexed and resuspended thoroughly. Eighteen microliters of each sample was mixed with an equal volume of latex sphere standard containing solution, in separate microfuge tubes (110 nM diameter latex spheres; 1.5×1010 particles per milliliter; Structure Probe Inc., West Chester, Pa.). The virus particle/latex sphere mixtures were diluted in ultrapure water at a 1:10 dilution in separate microfuge tubes, and vortexed and resuspended thoroughly. To prepare the grids, 300 mesh copper grids, coated with formvar and carbon were clasped tightly and secured with forceps. Each grid was rinsed with 0.01% bovine serum albumin and the excess solution wicked off using filter paper. Each sample was diluted in ultrapure water, ranging from 1:3 to 1:15 in varying dilutions. A 2.5 microliter aliquot of each diluted sample was placed on separate grids and allowed to air dry for approximately five minutes. After five minutes, any excess material was wicked off the grids using filter paper. After each grid had completely air-dried, the samples were fixed and stained with 20 microliters of 2.0% aqueous phosphotungstic acid, which was placed onto each grid and allowed to incubate for 30 seconds. Any excess stain was removed with filter paper. Each sample was intensively examined and total virus particles were counted using a Hitachi HU-12A Transmission Electron Microscope.

Description of General Steps in Vaccine Production

For ease in discussion and description, the various steps of vaccine composition production in general, can be thought of as comprising or falling into four broad groups. The first group comprises such aspects as co-infection, reassortment, selection of reassortants, and cloning of reassortants. The second group comprises such aspects as purification and expansion of reassortants. The third group comprises further expansion of reassortants in eggs or other host cells (e.g., MDCK and Vero), along with harvesting and purification of such harvested virus solutions. The fourth group comprises stabilization of harvested virus solutions and potency/sterility assays of the virus solutions. It is to be understood, however, that division of the aspects of the invention into the above four general categories is solely for explanatory/organizational purposes and no inference of interdependence of steps, etc. should be made. Again, it will be appreciated that other steps (both similar and different) are optionally used with the methods of the invention (e.g., the methods for incubation, e.g., secondary egg incubation, at 31° C.).

As mentioned above, for ease in discussion and description, the various steps of vaccine production can be thought of as comprising four broad groups. The first group comprises such aspects as co-infection, reassortment, selection of reassortants, and cloning of reassortants Group 1

The aspects of vaccine composition production which are broadly classified herein as belonging to Group 1 comprise methods and compositions related to optimization of co-infection of cell culture lines, e.g., with a master donor virus and one or more wild-type viruses in order to produce specifically desired reassorted viruses; selection of appropriate reassorted viruses; and cloning of the selected reassorted viruses. Reassortment of influenza virus strains is well known to those of skill in the art. Reassortment of both influenza A virus and influenza B virus has been used both in cell culture and in eggs to produce reassorted virus strains. See, e.g., Tannock et al., *Preparation and characterisation of attenuated cold-adapted influenza A reassortants derived from the A/Leningrad/134/17/57 donor strain, Vaccine* (2002) 20:2082-2090. Reassortment of influenza strains has also been shown with plasmid constructs. See, e.g., PCT Publications WO 03/091401, cited above.

Reassortment, in brief, generally comprises mixing (e.g., in eggs or cell culture) of gene segments from different viruses. For example, the typical 8 segments of influenza B virus strains can be mixed between, e.g., a wild-type strain having an epitope of interest and a "donor" strain, e.g., comprising a cold-adapted strain. Reassortment between the two virus types can produce, inter alia, viruses comprising the wild-type epitope strain for one segment, and the cold-adapted strain for the other segments. Unfortunately, to create the desired reassortants, a sometimes large number of reassortments need to be done. After being reassorted, the viruses can also be selected (e.g., to find the desired reassortants). The desired reassortants can then be cloned (e.g., expanded in number).

Traditional optimization, selection, and cloning of desired reassortants for influenza B virus, typically occurs by co-infection of virus strains into a cell culture (e.g., CEK cells) followed by selection with appropriate antibodies, e.g., against material from one of the parent virus, (usually done in eggs), and cloning or expanding of virus, etc. which is typically done in cell culture. However, such traditional reassortment presents drawbacks in that thousands of reassortments are needed to create the desired segment mix. When such reassortments are done, it is apparent that truly random reassortments are not the end result. In other words, pressures that bias the process exist in the systems. For influenza A strains, however, such processes do not appear to have such bias. For A strains, co-infection of strains (typically into cell culture such as CEK cells) is followed by selection and cloning at the same time, again, typically in cell culture.

Optimization of Reassortment

Various embodiments utilizing the steps in Group 1 can optimize the reassortment process in order to reduce the number of reassortments needed (and thus increase the throughput/stability of the vaccine production process), etc. The steps utilizing such optimization techniques are typically embodied with reassortment of influenza B strains and are typically done in cell culture, e.g., CEK cells. See, e.g., PCT Publication WO 05/014862.

Other methods of reassortment of influenza virus can optionally mix dilutions of a master donor virus (MDV) and a wild-type virus, e.g., a 1:5 dilution of each no matter the concentration of the respective solutions, which are then incubated for 24 and 48 hours at 25° C. and 33° C. While such an approach is often acceptable for influenza A strains, influenza B strains do not typically give positive results with such protocol. For example, to achieve the proper 6:2 assortment (i.e., 6 genes from the MDV and 2 genes, NA and HA from the wild-type virus) thousands of reassortments must often be done.

Selection and Cloning of Reassortments

The steps in Group 1 also comprise selection of reassorted influenza viruses. Reassorted influenza A strains are capable of selection in either cell culture (e.g., CEK cells) or in eggs. However, reassorted influenza B strains present problems when reassorted in cell culture (e.g., when selected for in CEK cells). It is believed that CEK cells interfere with the M gene in influenza B strains, thus reducing the overall production. Various methods of vaccine composition production, see, e.g., PCT Publication WO 05/014862, utilize different steps for virus reassortment, e.g., selection, etc. such various steps can optionally be used to create virus for the vaccine compositions, etc., herein.

Characterization of Reassortments

Yet other methods of virus/vaccine production utilize applications of a high throughput single strand conformation polymorphism/capillary electrophoresis (SSCP/CE) assay to determine the gene constellation of influenza viruses used herein. Influenza viruses contain 8 gene segments and, as described above, co-infection of a single cell with two different influenza strains can produce reassortant viruses with novel gene constellations distinct from either parent. Thus, some methods can use a SSCP/CE assay to rapidly determine the gene segment constellation of a large number of influenza virus samples. The influenza viral gene segments are optionally amplified by RT-PCR using fluorescent-labeled primers specific for each of the eight segments. See, also, Arvin et al. (2000) *J. Clin. Micro.* 38(2):839-845.

Prevention of Bacterial Contamination

Some methods of virus/vaccine production can comprise steps to detect and/or prevent/detect microbial contamination of eggs or other host cell cultures in which influenza virus is produced. The microbial detection strategies of the invention are useful for rapid/high throughput microbial detection and, thus, as with many other steps, are useful for increasing throughput and increased production in virus/vaccine production.

Many current influenza vaccine production strategies, which can optionally be used with the invention herein, use as a component, the traditional method for influenza virus expansion in specific-pathogen-free fertile chicken eggs. Possible microbial contamination can occur in several points in the production of virus in eggs. Unfortunately, the chicken eggs may have some microorganisms outside of their shells as part of their natural flora. It is also possible to have microorganisms enclosed within the shell of the egg during the development of the chicken embryo. Fertilized chicken eggs are incubated at 37° C. in high humidity for development of the embryo, which constitutes prime incubation conditions for many types of microbial contaminants as well. Another possible time of microbial contamination occurs when the shell is punctured to inoculate the egg. Even though prior to virus inoculation, the eggs are often sprayed with alcohol, there is still opportunity for microorganisms to enter into the egg.

After expansion of viruses for 2 to 3 days in the eggs, the top of the eggshell is typically removed for manual harvesting of the allantoic fluid containing virus within the egg. See, above. This harvesting is another point where microbial contamination may originate. Unfortunately eggs with such contaminating bioburden may escape detection, necessitating pooling into multiple bottles to minimize the rejection of the entire lot due to a failed MPA test. Since three influenza strains are typically used in vaccine production, blending of the three strains is required for the final bulk. In-process MPA (microbiological purity assay) testing is performed, e.g., at virus harvest prior to use in the blending and filling to ensure microbial-free product.

After incubation, the "traditional" method of candling is used to identify infertile and dead eggs that are possibly dead due to natural causes or to microbial contamination (i.e., dead eggs may occur due to infectivity of the virus and/or expansion of microorganisms, both of which require detection and removal of such eggs). Candling comprises, e.g., the process of holding an egg in front of a light source in a darkened room to enable visualization of the developing embryo. Dead eggs are excluded from virus inoculation.

Additionally, microbial contamination can occur in several points in the production of virus in cell culture, for example, if the starting host cell may be infected by a microbe prior to the initial culturing of the host cells. The preparation of a master cell bank (MCB) is essential for use in the production of virus for vaccine material. The MCB is extensively tested to ensure that there is no evidence of microbial agents, optionally the MCB may be tested for tumorigenicity and/or oncogenicity. Alternatively microorganisms may be introduced during any step which requires opening of the growth vessel (e.g., fermenter) used to culture the host cells. Steps which may require the opening of the growth vessel include, for example, during any addition of protease or other supplement to the culture and during viral infection of the host cells. The use of sterile media and facilities combined with the development of procedures designed to minimize opening of the growth vessel are essential to minimized the risk of contamination.

As can be seen from the above points, detection of microbial contamination can be needed at multiple steps during the manufacture of influenza vaccine. There is a need to eliminate or reduce avian and environmental microbes and a need to eliminate or reduce introduction of environmental and human microbes. Current methods for detection of contaminating microorganisms include, e.g., compendial methods (MPA and Bioburden). Current methods can include, e.g., egg candling during egg pre/post inoculation (which is typically done manually at a rate of about 500 eggs/hour/person); MPA and BioBurden tests which are typically manual and take about 14 days for MPA and about 3 days for BioBurden (which are done during the preparation of a MCB and virus harvest); mycoplasma testing; which is typically done manually and takes about 28 days (done during virus harvest); and mycobacterium testing which is typically manual and takes about 56 days (done during virus harvest). Again, see, e.g., PCT Publication WO 05/014862, for descriptions of various techniques capable of use with the current invention.

Group 2

Aspects of virus/vaccine production that fall into Group 2 include further purification and virus expansion, etc. After the process of correct reassortment and cloning of reassortants (e.g., the 6:2 viruses), such reassorted virus particles are further purified in embryonated hen eggs and the correct clones are expanded in quantity (again through growth in hen eggs) to generate a master virus strain (MVS) or master virus seed, which, in turn, is further expanded to generate a master working virus strain (MWVS) or manufacturer's working virus seed. Many aspects of purification of virus particles from eggs and use of such purified virus to inoculate more eggs in order to expand the quantity of virus particles are well known to those skilled in the art. Many such techniques are common in the current production of virus particles and have been used for at least 40 years. See, e.g., Reimer, et al. *Influenza virus purification with the zonal ultracentrifuge, Science* 1966, 152:1379-81. Purification protocols can involve, e.g., ultra-centrifugation in sucrose gradients (e.g., 10-40% sucrose), etc. Also, as noted herein, other procedures, etc. listed in other Groups are also optionally present within Group 2, e.g., prevention of microbial contamination, etc.

Group 3

Aspects of virus/vaccine production that fall under the heading of Group 3 include, e.g., conditioning of the embryonated eggs or other host cells (e.g., specific handling and environmental conditions involved in the incubation of virus infected eggs or other host cells) and the harvesting and clarification of influenza virus from the allantoic fluid of the eggs or the culture supernatant of the host cells.

For example, conditioning, washing, candling, and incubating eggs which contain the reassorted virus to be used in a vaccine; inoculation, sealing, etc. of such eggs; candling of such eggs; harvesting of the virus solution (e.g., the allantoic fluid) from the eggs; culturing and inoculation of host cells; harvesting of the virus solution (e.g., the cell culture supernatant) from the host cells; and clarification of the virus solution can all fall within such category. Again, it should be noted that several techniques applicable to the steps in Groups 2 are equally applicable to the steps in Group 3 (e.g., candling, etc.). Several aspects of virus/vaccine production that comprise Groups 3 are well known to those skilled in the art. Various aspects of candling of eggs in virus production, as well as inoculation of eggs with viruses and washing, incubating, etc. of such eggs are well known techniques in the production of virus/vaccines in eggs. Of course, it will be appreciated that such well-known techniques are used in conjunction with the unique and innovate aspects of the current invention. Again, PCT Publication WO 05/014862, gives further steps such as rocking, etc. that can also be used with the methods and compositions of the current invention. Other similar steps can include specific filtering and warming of compositions, again, see, PCT Publication WO 05/014862.

Filtering and Warming

Again, PCT Publication WO 05/014862 also gives other filtering and warming steps that can optionally be used with the methods and compositions of the current invention. As described, the FluMist™ manufacturing process can use embryonated chicken eggs to generate master virus seeds (MVS), manufacturer's working virus seeds (MWVS) and virus harvests (VH). The seeds and viral harvest may contain bioburden (typically bacterial contamination), which would cause the seed or bulk virus product lots to be rejected in the vaccine production process. Of course, it will be appreciated that specific listing or description of particular product types used, sizes, etc., is not to be considered limiting on the current invention unless specifically stated to be so.

Group 4

Group 4 of the aspects of vaccine production comprises, e.g., steps primarily concerned with stabilization (e.g., through addition of components, alterations in buffer/NAF ratios, etc.) and assays of potency/sterility of virus containing solutions. In some embodiments, the final viral solutions/vaccines of the invention can comprise live viruses that are stable in liquid form for a period of time sufficient to allow storage "in the field" (e.g., on sale and commercialization when refrigerated at 2-8° C., 4° C., 5° C., etc.) throughout an influenza vaccination season (e.g., typically from about September through March in the northern hemisphere). Thus, the virus/vaccine compositions are desired to retain their potency or to lose their potency at an acceptable rate over the storage period. In other embodiments, such solutions/vaccines are stable in liquid form at from about 2° C. to about 8° C., e.g., refrigerator temperature. Thus, the virus/vaccine produced via the current invention and the methods of the current invention can be produced by and/or used with such procedures, etc. Again, see PCT Publication WO 05/014862.

Concentration/Diafiltration of Virus Harvests

In some methods of vaccine composition production, virus harvests are optionally concentrated using a appropriate column. See, PCT Publication WO 05/014862.

Stabilizers/Buffers

Vaccine composition production can also optionally include various dilutions of NAF (typically unfractionated NAF) comprising the virus of interest and combinations of, e.g., sucrose, arginine, gelatin, EDTA, etc. See, e.g., PCT Publication WO 05/014862, for examples of various combinations possible in different vaccine formulations. Such methods and compositions are in certain embodiments, stable (i.e., do not show unacceptable losses in potency) over selected time periods (typically at least 6 months, at least 9 months, at least 12 months, at least 15 months, at least 18 months, at least 24 months, etc.) at desired temperatures (e.g., typically 4° C., 5° C., 8° C., from about 2° C. to about 8° C. or greater than 2° C., etc.).

In some formulations, compositions can comprise a stabilizer of, e.g., arginine (of pH from about 7.0 to about 7.2) either in combination with, or in place of gelatin or gelatin related and/or derived products (e.g., gelatin hydrosylate). Again, see PCT Publication WO 05/014862. Also, in many virus solutions/vaccine solutions a base solution of SPG (sucrose, potassium phosphate and monosodium glutamate) is optionally utilized.

Again, PCT Publication WO 05/014862 gives other/additional methods of virus/vaccine composition stabilization, e.g., NAF level manipulation, etc.

DEFINITIONS

Unless defined otherwise, all scientific and technical terms are understood to have the same meaning as commonly used in the art to which they pertain. For the purpose of the present invention the following terms are defined below.

The terms "nucleic acid," "polynucleotide," "polynucleotide sequence" and "nucleic acid sequence" refer to single-stranded or double-stranded deoxyribonucleotide or ribonucleotide polymers, or chimeras or analogues thereof. As used herein, the term optionally includes polymers of analogs of naturally occurring nucleotides having the essential nature of natural nucleotides in that they hybridize to single-stranded nucleic acids in a manner similar to naturally occurring nucleotides (e.g., peptide nucleic acids). Unless otherwise indicated, a particular nucleic acid sequence optionally encompasses complementary sequences, in addition to the sequence explicitly indicated.

The term "gene" is used broadly to refer to any nucleic acid associated with a biological function. Thus, genes include coding sequences and/or the regulatory sequences required for their expression. The term "gene" applies to a specific genomic sequence, as well as to a cDNA or an mRNA encoded by that genomic sequence.

Genes also include non-expressed nucleic acid segments that, for example, form recognition sequences for other proteins. Non-expressed regulatory sequences include "promoters" and "enhancers," to which regulatory proteins such as transcription factors bind, resulting in transcription of adjacent or nearby sequences. A "tissue specific" promoter or enhancer is one that regulates transcription in a specific tissue type or cell type or types.

The term "vector" refers to the means by which a nucleic acid can be propagated and/or transferred between organisms, cells, or cellular components. Vectors include plasmids, viruses, bacteriophage, pro-viruses, phagemids, transposons, and artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not autonomously replicating.

An "expression vector" is a vector, such as a plasmid, that is capable of promoting expression of, as well as replication of, a nucleic acid incorporated therein. Typically, the nucleic acid to be expressed is "operably linked" to a promoter and/or enhancer, and is subject to transcription regulatory control by the promoter and/or enhancer.

A "bi-directional expression vector" is characterized by two alternative promoters oriented in the opposite direction relative to a nucleic acid situated between the two promoters, such that expression can be initiated in both orientations resulting in, e.g., transcription of both plus (+) or sense strand, and negative (−) or antisense strand RNAs.

In the context herein, the term "isolated" refers to a biological material, such as a nucleic acid or a protein, which is substantially free from components that normally accompany or interact with it in its naturally occurring environment. The isolated material optionally comprises material not found with the material in its natural environment, e.g., a cell. For example, if the material is in its natural environment, such as a cell, the material has been placed at a location in the cell (e.g., genome or genetic element) not native to a material found in that environment. For example, a naturally occurring nucleic acid (e.g., a coding sequence, a promoter, an enhancer, etc.) becomes isolated if it is introduced by non-naturally occurring means to a locus of the genome (e.g., a vector, such as a plasmid or virus vector, or amplicon) not native to that nucleic acid. Such nucleic acids are also referred to as "heterologous" nucleic acids.

The term "recombinant" indicates that the material (e.g., a nucleic acid or protein) has been artificially or synthetically (non-naturally) altered. The alteration can be performed on the material within, or removed from, its natural environment or state. Specifically, when referring to a virus, e.g., an influenza virus, is recombinant when it is produced by the expression of a recombinant nucleic acid.

The term "reassortant," when referring to a virus, indicates that the virus includes genetic and/or polypeptide components derived from more than one parental viral strain or source. For example, a 7:1 reassortant includes 7 viral genomic segments (or gene segments) derived from a first parental virus, and a single complementary viral genomic segment, e.g., encoding hemagglutinin or neuraminidase, from a second parental virus. A 6:2 reassortant includes 6 genomic segments, most commonly the 6 internal genes from a first parental virus, and two complementary segments, e.g., hemagglutinin and neuraminidase, from a different parental virus.

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such methods as "infection," "transfection," "transformation," and "transduction." In the context of the invention, a variety of methods can be employed to introduce nucleic acids into prokaryotic cells, including electroporation, calcium phosphate precipitation, lipid mediated transfection (lipofection), etc.

The term "host cell" means a cell that contains a heterologous nucleic acid, such as a vector, and supports the replication and/or expression of the nucleic acid. Host cells can be prokaryotic cells such as E. coli, or eukaryotic cells such as yeast, insect, amphibian, avian or mammalian cells, including human cells. Exemplary host cells in the context of the invention include Vero (African green monkey kidney) cells, BHK (baby hamster kidney) cells, primary chick kidney (PCK) cells, Madin-Darby Canine Kidney (MDCK) cells, Madin-Darby Bovine Kidney (MDBK) cells, 293 cells (e.g., 293T cells), and COS cells (e.g., COS1, COS7 cells).

Influenza Virus

The compositions and methods herein are primarily concerned with production of influenza viruses for vaccines. Influenza viruses are made up of an internal ribonucleoprotein core containing a segmented single-stranded RNA genome and an outer lipoprotein envelope lined by a matrix protein. Influenza A and influenza B viruses each contain eight segments of single stranded negative sense RNA. The influenza A genome encodes eleven polypeptides. Segments 1-3 encode three polypeptides, making up a RNA-dependent RNA polymerase. Segment 1 encodes the polymerase complex protein PB2. The remaining polymerase proteins PB1 and PA are encoded by segment 2 and segment 3, respectively. In addition, segment 1 of some influenza strains encodes a small protein, PB1-F2, produced from an alternative reading frame within the PB1 coding region. Segment 4 encodes the hemagglutinin (HA) surface glycoprotein involved in cell attachment and entry during infection. Segment 5 encodes the nucleocapsid nucleoprotein (NP) polypeptide, the major structural component associated with viral RNA. Segment 6 encodes a neuraminidase (NA) envelope glycoprotein. Segment 7 encodes two matrix proteins, designated M1 and M2, which are translated from differentially spliced mRNAs. Segment 8 encodes NS1 and NS2, two nonstructural proteins, which are translated from alternatively spliced mRNA variants.

The eight genome segments of influenza B encode 11 proteins. The three largest genes code for components of the RNA polymerase, PB1, PB2 and PA. Segment 4 encodes the HA protein. Segment 5 encodes NP. Segment 6 encodes the NA protein and the NB protein. Both proteins, NB and NA, are translated from overlapping reading frames of a biscistronic mRNA. Segment 7 of influenza B also encodes two proteins: M1 and BM2. The smallest segment encodes two products, NS1 which is translated from the full length RNA, and NS2 which is translated from a spliced mRNA variant.

Influenza Virus Vaccine

Historically, influenza virus vaccines have primarily been produced in embryonated hen eggs using strains of virus selected based on empirical predictions of relevant strains. More recently, reassortant viruses have been produced that incorporate selected hemagglutinin and neuraminidase antigens in the context of an approved attenuated, temperature sensitive master strain. Following culture of the virus through multiple passages in hen eggs, influenza viruses are recovered and, optionally, inactivated, e.g., using formaldehyde and/or β-propiolactone (or alternatively used in live attenuated vaccines).

However, production of influenza vaccine in this manner has several significant concerns. For example, contaminants remaining from the hen eggs can be highly antigenic and/or pyrogenic, and can frequently result in significant side effects upon administration. Thus, another method involves replacement of some percentage of egg components with animal free media. More importantly, virus strains designated for vaccine production must be selected and distributed, typically months in advance of the next flu season to allow time for production and inactivation of influenza vaccine. Again, any improvements in stability in storage time and/or of storage at a more convenient temperature (e.g., refrigerator temperature of about 2-8° C.), e.g., in order to decrease product loss, are thus quite desirable.

Attempts at producing recombinant and reassortant vaccines in cell culture have been hampered by the inability of some of the strains approved for vaccine production to grow efficiently under standard cell culture conditions. Thus, prior work by the inventor and his coworkers provided a vector system, and methods for producing recombinant and reassortant viruses in culture, thus, making it possible to rapidly produce vaccines corresponding to one or many selected antigenic strains of virus. See, e.g., PCT Publications WO 03/091401, cited above. Of course, such reassortments are optionally further amplified in hen eggs. Typically, the cultures are maintained in a system, such as a cell culture incubator, under controlled humidity and $CO_2$, at constant temperature using a temperature regulator, such as a thermostat to insure that the temperature does not exceed 35° C. Such pioneering work, as well as other vaccine production, can be further optimized through use of the current invention in whole or part.

Reassortant influenza viruses can be readily obtained by introducing a subset of vectors (e.g., viruses, plasmids, etc.) corresponding to genomic segments of a master influenza virus, in combination with complementary segments derived from strains of interest (e.g., antigenic variants of interest). Typically, the master strains are selected on the basis of desirable properties relevant to vaccine administration. For example, for vaccine production, e.g., for production of a live attenuated vaccine, the master donor virus strain may be selected for an attenuated phenotype, cold adaptation and/or temperature sensitivity.

FluMist®

As mentioned previously, numerous examples and types of influenza vaccine exist. An exemplary influenza vaccine is FluMist which is a live, attenuated vaccine that protects children and adults from influenza illness (Belshe et al. (1998) *The efficacy of live attenuated, cold-adapted, trivalent, intranasal influenza virus vaccine in children N. Engl. J. Med.* 338:1405-12; Nichol et al. (1999) *Effectiveness of live, attenuated intranasal influenza virus vaccine in healthy, working adults: a randomized controlled trial JAMA* 282: 137-44). In typical embodiments, the methods and compositions of the current invention are optionally adapted to, or used with, production of FluMist vaccine. However, it will be appreciated by those skilled in the art that the steps/compositions herein are also adaptable to production of similar or even different viral vaccines and their compositions.

FluMist™ vaccine strains contain, e.g., HA and NA gene segments derived from the wild-type strains to which the vaccine is addressed along with six gene segments, PB1, PB2, PA, NP, M and NS, from a common master donor virus (MDV). The MDV for influenza A strains of FluMist (MDV-A), was created by serial passage of the wild-type A/Ann Arbor/6/60 (A/AA/6/60) strain in primary chicken kidney tissue culture at successively lower temperatures (Maassab (1967) *Adaptation and growth characteristics of influenza virus at 25 degrees C Nature* 213:612-4). MDV-A replicates efficiently at 25° C. (ca, cold adapted), but its growth is restricted at 38 and 39° C. (ts, temperature sensitive). Additionally, this virus does not replicate in the lungs of infected ferrets (att, attenuation). The ts phenotype is believed to contribute to the attenuation of the vaccine in humans by restricting its replication in all but the coolest regions of the respiratory tract. The stability of this property has been demonstrated in animal models and clinical studies. In contrast to the ts phenotype of influenza strains created by chemical mutagenesis, the ts property of MDV-A does not revert following passage through infected hamsters or in shed isolates from children (for a recent review, see Murphy & Coelingh (2002) *Principles underlying the development and use of live attenuated cold-adapted influenza A and B virus vaccines Viral Immunol.* 15:295-323).

Clinical studies in over 20,000 adults and children involving 12 separate 6:2 reassortant strains have shown that these vaccines are attenuated, safe and efficacious (Belshe et al. (1998) *The efficacy of live attenuated, cold-adapted, trivalent, intranasal influenza virus vaccine in children N. Engl. J. Med.* 338:1405-12; Boyce et al. (2000) *Safety and immunogenicity of adjuvanted and unadjuvanted subunit influenza vaccines administered intranasally to healthy adults Vaccine* 19:217-26; Edwards et al. (1994) *A randomized controlled trial of cold adapted and inactivated vaccines for the prevention of influenza A disease J. Infect. Dis.* 169:68-76; Nichol et al. (1999) *Effectiveness of live, attenuated intranasal influenza virus vaccine in healthy, working adults: a randomized controlled trial JAMA* 282:137-44). Reassortants carrying the six internal genes of MDV-A and the two HA and NA gene segments of a wild-type virus (i.e., a 6:2 reassortant) consistently maintain ca, ts and att phenotypes (Maassab et al. (1982) *Evaluation of a cold-recombinant influenza virus vaccine in ferrets J. Infect. Dis.* 146:780-900). Production of such reassorted virus using B strains of influenza is more difficult, however.

Recent work, see, e.g., PCT Publications WO 03/091401, cited above, has shown an eight plasmid system for the generation of influenza B virus entirely from cloned cDNA, and methods for the production of attenuated live influenza A and B virus suitable for vaccine formulations, such as live virus vaccine formulations useful for intranasal administration. The current invention also presents improved methods of B strain production.

The system and methods described previously are useful for the rapid production of recombinant and reassortant influenza A and B viruses, including viruses suitable for use as vaccines, including live attenuated vaccines, such as vaccines suitable for intranasal administration such as FluMist®. The methods of the current invention herein, are optionally used in conjunction with or in combination with such previous work involving, e.g., reassorted influenza viruses for vaccine production to produce viruses for vaccines in a more stable, consistent and productive manner.

Viral Replication in Cell Culture

As previously stated, influenza virus optionally can be grown in cell culture. Typically, propagation of the virus is accomplished in the media compositions in which the host cell is commonly cultured. Suitable host cells for the replication of influenza virus include, e.g., Vero cells, BHK cells, MDCK cells, 293 cells and COS cells, including 293T cells, COS7 cells. Commonly, co-cultures including two of the above cell lines, e.g., MDCK cells and either 293T or COS cells are employed at a ratio, e.g., of 1:1, to improve replication efficiency. Typically, cells are cultured in a standard commercial culture medium, such as Dulbecco's modified Eagle's medium supplemented with serum (e.g., 0.5-10% fetal bovine serum), or in serum free medium (e.g. Iscove's medium, ultra CHO medium (BioWhittaker), EX-CELL (JRH Biosciences)), or animal protein-free media (e.g. PF-CHO (JRH Biosciences), under controlled humidity and $CO_2$ concentration suitable for maintaining neutral buffered pH (e.g., at pH between 7.0 and 7.2). Optionally, the medium contains antibiotics to prevent bacterial growth, e.g., penicillin, streptomycin, etc., and/or additional nutrients, such as L-glutamine, sodium pyruvate, non-essential amino acids, additional supplements to promote favorable growth characteristics, e.g., trypsin, β-mercaptoethanol, and the like.

Procedures for maintaining mammalian cells in culture have been extensively reported, and are well known to those of skill in the art. General protocols are provided, e.g., in Freshney (1983) *Culture of Animal Cells: Manual of Basic Technique*, Alan R. Liss, New York; Paul (1975) *Cell and Tissue Culture,* 5$^{th}$ ed., Livingston, Edinburgh; Adams (1980) *Laboratory Techniques in Biochemistry and Molecular Biology-Cell Culture for Biochemists*, Work and Burdon (eds.) Elsevier, Amsterdam. Additional details regarding tissue culture procedures of particular interest in the production of influenza virus in vitro include, e.g., Merten et al. (1996) *Production of influenza virus in cell cultures for vaccine preparation* in Cohen and Shafferman (eds.) *Novel Strategies in Design and Production of Vaccines*. Additionally, variations in such procedures adapted to the present invention are readily determined through routine experimentation and will be familiar to those skilled in the art.

Cells for production of influenza virus can be cultured in serum-containing or serum free or animal protein free medium. In some cases, e.g., for the preparation of purified viruses, it is typically desirable to grow the host cells in serum free or animal protein free conditions. Cells may be cultured as adherent cells on a substrate (e.g., microcarrier) or as a cell suspension without adhering to any substrate. Cells can be cultured in small scale, e.g., less than 25 ml medium, culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

Regardless of the culture volume, in many desired aspects, it is important that the cultures be maintained at an appropriate temperature, to insure viral replication and/or efficient recovery of recombinant and/or reassortant influenza virus using temperature dependent multi plasmid systems (see, e.g., e.g., PCT Publications WO 03/091401, cited above), heating of virus solutions for filtration, etc. Typically, a regulator, e.g., a thermostat, or other device for sensing and maintaining the temperature of the cell culture system and/or other solution, is employed to insure that the temperature is at the correct level during the appropriate period (e.g., virus replication, etc.).

In some methods (e.g., wherein reassorted viruses are to be produced from segments on vectors) vectors comprising influenza genome segments are introduced (e.g., transfected) into host cells according to methods well known in the art for introducing heterologous nucleic acids into eukaryotic cells, including, e.g., calcium phosphate co-precipitation, electroporation, microinjection, lipofection, and transfection employing polyamine transfection reagents. For example, vectors, e.g., plasmids, can be transfected into host cells, such as COS cells, 293T cells or combinations of COS or 293T cells and MDCK cells, using the polyamine transfection reagent TransIT-LT1 (Mirus) according to the manufacturer's instructions in order to produce reassorted viruses, etc. Approximately 1 µg of each vector to be introduced into the population of host cells with approximately 2 µl of TransIT-LT1 diluted in 160 µl medium, preferably serum-free medium, in a total volume of 200 µl. The DNA:transfection reagent mixtures are incubated at room temperature for 45 minutes followed by addition of 800 µl of medium. The transfection mixture is added to the host cells, and the cells are cultured as described above or via other methods well known to those skilled in the art. Accordingly, for the production of recombinant or reassortant viruses in cell culture, vectors incorporating each of the 8 genome segments, (PB2, PB1, PA, NP, M, NS, HA and NA) are mixed with approximately 20 µl TransIT-LT1 and transfected into host cells. Optionally, serum-containing medium is replaced prior to transfection with serum-free medium, e.g., Opti-MEM I, and incubated for 4-6 hours.

Alternatively, electroporation can be employed to introduce such vectors incorporating influenza genome segments into host cells. See PCT Publication WO 05/062820. For example, plasmid vectors incorporating an influenza A or influenza B virus are favorably introduced into Vero cells using electroporation according to the following procedure. In brief, approximately $5 \times 10^6$ Vero cells, e.g., grown in Modified Eagle's Medium (MEM) supplemented with 10% Fetal Bovine Serum (FBS) are resuspended in 0.4 ml OptiMEM and placed in an electroporation cuvette. Twenty micrograms of DNA in a volume of up to 25 µl is added to the cells in the cuvette, which is then mixed gently by tapping. Electroporation is performed according to the manufacturer's instructions (e.g., BioRad Gene Pulser II with Capacitance Extender Plus connected) at 300 volts, 950 microFarads with a time constant of between 28-33 msec. The cells are remixed by gently tapping and, approximately 1-2 minutes following electroporation, 0.7 ml MEM with 10% FBS is added directly to the cuvette. The cells are then transferred to two wells of a standard 6 well tissue culture dish containing 2 ml MEM, 10% FBS. The cuvette is washed to recover any remaining cells and the wash suspension is divided between the two wells. Final volume is approximately 3.5 mL. The cells are then incubated under conditions permissive for viral growth, e.g., at approximately 33° C. for cold adapted strains.

In some methods (e.g., wherein the host cells is used for the production of virus for vaccine production) the host cells are cultured and infected with virus according to methods well known in the art. For example, the infection of the cultured cells is preferably carried out when the cells have achieved an optimum cell density (e.g., between about $5 \times 10^5$ to $20 \times 10^6$ cells/ml, depending on the culture conditions utilized). Host cells are infected at a multiplicity of infection (m.o.i.) of about 0.001 to about 10 (optionally, at an m.o.i. of about 0.002 to about 0.5). Generally, efficient replication of virus in an animal cells requires the addition of a protease (e.g., a serine protease, such as trypsin), optionally, protease may be added to the culture shortly before, simultaneously to or shortly after infection. According the present invention, following viral infection, the infected cells are further cultured to replicate the viruses at temperatures of less than 33° C., e.g., 31° C. (or optionally at between about 29° C. and about 32° C.), generally until a maximum cytopathic effect or a maximum amount of virus can be detected (e.g., $TCID_{50}$ assay and Q RT-PCR assay). Optionally, the culturing of the infected cells is carried out for about 2 to about 10 days. Specific methods useful for the produce virus-containing cell supernatants are known in the art (see, e.g., U.S. Pat. Nos. 4,500,513, 6,656,720, 6,455, 298 and 6,146,873). It will be appreciated that other steps (both similar and different) are optionally used with the methods of the invention.

Kits

To facilitate use of the methods and compositions of the invention, any of the vaccine components and/or compositions, e.g., virus in various formulations, etc., and additional components, such as, buffer, cells, culture medium, useful for packaging and infection of influenza viruses for experimental or therapeutic vaccine purposes, can be packaged in the form of a kit. Typically, the kit contains, in addition to the above components, additional materials which can include, e.g., instructions for performing the methods of the invention, packaging material, and a container.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method of increasing the yield of attenuated cold adapted reassortant influenza B virus particles, the method comprising:
    a. introducing a plurality of attenuated cold adapted reassortant influenza B viruses into SPF embryonated hen eggs;
    b. incubating the host eggs at a temperature of 31±0.5° C.; and,
    c. recovering influenza virus particles from the host eggs, wherein the recovered virus particles resulting from the incubation has a yield which is greater than the yield resulting from an incubation of said attenuated cold adapted reassortant influenza B viruses in host eggs at 33° C., and wherein said attenuated cold adapted reassortant influenza B viruses comprise a partial genome of the B/Ann Arbor/1/66 master donor virus.

2. The method of claim 1, wherein the yield is quantified by determining the $\log_{10}$ TCID$_{50}$/mL titer of allantoic fluid of the host eggs infected with the virus particles incubated at 31±0.5° C. and by determining the $\log_{10}$ TCID$_{50}$/mL titer of allantoic fluid of the host eggs infected with the virus particles incubated at 33° C.

3. The method of claim 2, wherein the $\log_{10}$ TCID$_{50}$/mL titer, from the incubation at 31±0.5° C. is from at least about 1.01 to at least about 1.10 times greater than the $\log_{10}$ TCID$_{50}$/mL titer at 33° C.

4. The method of claim 2, wherein the $\log_{10}$ TCID$_{50}$/mL titer, from the incubation at 31±0.5° C., is from at least about 1.025 to at least about 1.05 greater than the $\log_{10}$ TCID$_{50}$/mL titer at 33° C.

5. The method of claim 2, wherein the $\log_{10}$ TCID$_{50}$/mL titer, from the incubation at 31±0.5° C., is from at least about 1.03 to at least about 1.04 times greater, than the $\log_{10}$ TCID$_{50}$/mL titer at 33° C.

6. The method of claim 2, wherein the $\log_{10}$ TCID$_{50}$/mL titer, from the incubation at 31±0.5° C., is from at least about 0.2 to at least about 0.7 higher than the $\log_{10}$ TCID$_{50}$/mL titer at 33° C.

7. The method of claim 1, wherein said attenuated cold adapted reassortant influenza B virus is a 6:2 reassortant comprising six genome segments of the B/Ann Arbor/1/66 master donor virus.

8. The method of claim 2, wherein said attenuated cold adapted reassortant influenza B virus is a 6:2 reassortant comprising six genome segments of the B/Ann Arbor/1/66 master donor virus.

9. The method of claim 3, wherein said attenuated cold adapted reassortant influenza B virus is a 6:2 reassortant comprising six genome segments of the B/Ann Arbor/1/66 master donor virus.

10. The method of claim 4, wherein said attenuated cold adapted reassortant influenza B virus is a 6:2 reassortant comprising six genome segments of the B/Ann Arbor/1/66 master donor virus.

11. The method of claim 5, wherein said attenuated cold adapted reassortant influenza B virus is a 6:2 reassortant comprising six genome segments of the B/Ann Arbor/1/66 master donor virus.

12. The method of claim 6, wherein said attenuated cold adapted reassortant influenza B virus is a 6:2 reassortant comprising six genome segments of the B/Ann Arbor/1/66 master donor virus.

* * * * *